US012594344B2

(12) United States Patent
Chen et al.

(10) Patent No.: US 12,594,344 B2
(45) Date of Patent: Apr. 7, 2026

(54) PRODUCTION OF EXOSOMES AND USES THEREOF

(71) Applicants: CHINA MEDICAL UNIVERSITY, Taichung City (TW); China Medical University Hospital, Taichung City (TW); Shine-On Biomedical Co., Ltd., Taichung City (TW)

(72) Inventors: Yi-Wen Chen, Taichung City (TW); Der-Yang Cho, Taichung City (TW); Hsin-Yuan Fang, Taichung City (TW); Ming-You Shie, Taichung City (TW); Chih-Ming Pan, Taichung City (TW); Kai-Wen Kan, Taichung City (TW); Cheng-Yu Chen, Taichung City (TW); Min-Hua Yu, Taichung City (TW); Shao-Chih Chiu, Taichung City (TW)

(73) Assignees: China Medical University, Taichung City (TW); China Medical University Hospital, Taichung City (TW); Shine-On Biomedical Co., Ltd., Taichung City (TW)

( * ) Notice: Subject to any disclaimer, the term of this patent is extended or adjusted under 35 U.S.C. 154(b) by 668 days.

(21) Appl. No.: 18/060,966

(22) Filed: Dec. 2, 2022

(65) Prior Publication Data

US 2023/0211009 A1      Jul. 6, 2023

Related U.S. Application Data

(60) Provisional application No. 63/285,493, filed on Dec. 3, 2021.

(51) Int. Cl.
*A61K 47/69* (2017.01)
*A61P 35/00* (2006.01)

*C07K 14/705* (2006.01)
*C07K 16/28* (2006.01)
*C12N 5/071* (2010.01)

(52) U.S. Cl.
CPC .......... *A61K 47/6901* (2017.08); *A61P 35/00* (2018.01); *C07K 14/70596* (2013.01); *C07K 16/2833* (2013.01); *C12N 5/0686* (2013.01); *C07K 2317/569* (2013.01); *C07K 2319/03* (2013.01); *C12N 2527/00* (2013.01)

(58) Field of Classification Search
CPC ................ A61K 47/6901; A61P 35/00; C07K 14/70596; C07K 16/2833; C07K 2317/569; C07K 2319/03; C12N 5/0686; C12N 2527/00
See application file for complete search history.

(56) References Cited

PUBLICATIONS

Nail et al. Exosomal miRNA-mediated intercellular communications and immunomodulatory efects in tumor microenvironments. J Biomed Sci 30, 69: 1-23, published Aug. 21, 2023.*

* cited by examiner

*Primary Examiner* — Alana Harris Dent
(74) *Attorney, Agent, or Firm* — Hannah Tien

(57) ABSTRACT

A method for producing exosomes in a large-scale by using a cyclic tensile bioreactor to stimulate cells to release exosomes. In addition, the exosome having an anti-HLA-G protein specific for cancer is used as a delivery vehicle to deliver therapeutic agents for treating cancer.

10 Claims, 20 Drawing Sheets
(9 of 20 Drawing Sheet(s) Filed in Color)
Specification includes a Sequence Listing.

YZ section image

CARExo        miR-34a        miR-34a@CARExo

Figure 16B                    Figure 16C

PRODUCTION OF EXOSOMES AND USES THEREOF

This application claims the benefit of U.S. Provisional Patent Application No. 63/285,493 filed on Dec. 3, 2021, which is incorporated by reference herein in its entirety.

This application contains a Sequence Listing in a computer readable form, the file name is 4020-CMU-SEQList-1129, created on Nov. 29, 2022, the size is 4 KB, which is incorporated herein by reference.

FIELD OF THE INVENTION

The present invention is related to a method for producing exosomes in a large scale by using a cyclic tensile bioreactor to stimulate cells to release exosomes. In addition, the present invention relates to an exosome with anti-HLA-G protein specific for cancer.

DESCRIPTION OF PRIOR ART

In recent years, various pharmaceutical companies have been put abounded resources in developing novel drug carriers, which expected to deliver small molecule or biologics drugs more efficiently and precisely. Due to exosome's low immunogenicity, good biocompatibility, biological activity, low rejection to cells, and nano-size to microenvironment, it has been considered to be extraordinary candidate of drug carrier. Not only the previous advantages, exosomes own other remarkable properties such as high affinity, easy to be phagocytosed by target cells, easy to degrade and release drugs in cells, and avoid being consumed by the immune system.

SUMMARY OF THE INVENTION

The present invention provides a method for promoting production of exosomes, which comprises: (a) providing a cyclic tensile bioreactor, wherein the cyclic tensile bioreactor comprises a culture chamber, a biocompatible polymeric material with an auxetic structure and a plurality of tensile components, the biocompatible polymeric material and the plurality of tensile components are placed in the culture chamber, the biocompatible polymeric material comprises exosome-producing cells, and two ends of the biocompatible polymeric material are connected with the plurality of tensile components; (b) repeatedly stretching the biocompatible polymeric material by using the plurality of tensile components to apply cyclic tensile force; and (c) collecting the exosomes which are released from the exosome-producing cells by cyclic tensile force applied by the plurality of tensile components.

The present invention also provides an exosome, which comprises a fusion protein, wherein the fusion protein comprises a targeting protein and an exosomal transmembrane protein, and the targeting protein comprises an anti-HLA-G protein. The present invention further provides a method for treating a subject with cancer, comprising administering a composition into the subject with cancer, wherein the composition comprises a therapeutic exosome, and the therapeutic exosome comprises the above fusion protein and an anti-cancer agent.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows the verification of morphology of exosome with/without cargo engineering. FIG. 1B shows the verification of size of exosome with/without cargo engineering. Exo: exosomes; and CARExo: cargo exosomes.

FIG. 2A shows the identification of the biomarkers (CD63, CD81, CD9, Alix, HSP-70 and β-tubulin) of exosomes by using west blot. FIG. 2B shows the identification of the biomarkers (CD63, CD81, and CD9) of exosomes by using flow cytometry. PE-A: phycoerythrin area.

FIG. 12A shows the validation of the efficacy of miRNA/DOX-loaded CARExo in inhibiting breast cancer tumors in vivo. FIG. 12B shows evaluating the efficacy of miRNA/DOX-loaded CARExo in tumor metastasis of other organs. Ctl: Control.

FIGS. 16A-16C show the preparation of the cell-laden FGelMa hydrogel and the using of cyclic stretch culture system. FIG. 16A shows the scheme illustrating the procedures used to prepare the cell-laden auxetic hydrogels. FIG. 16B shows the as-prepared auxetic hydrogel is immersed in the culture medium. FIG. 16C shows that the cell-laden auxetic hydrogels is applied to the dynamic tensile culture system, and consequently cultured under cyclic stretching at a strain of 20% and a frequency of 0.48 Hz.

FIG. 19A shows the differences in cell morphology and YAP protein staining of HEK293T-laden auxetic scaffolds with YAP inhibitor (Verteporfin) in a cyclic tensile culture system. FIG. 19B shows the differences in exosome secretion of HEK293T-laden auxetic scaffolds with YAP inhibitor (Verteporfin) in a cyclic tensile culture system.

DETAILED DESCRIPTION OF THE INVENTION

Figure 1A:
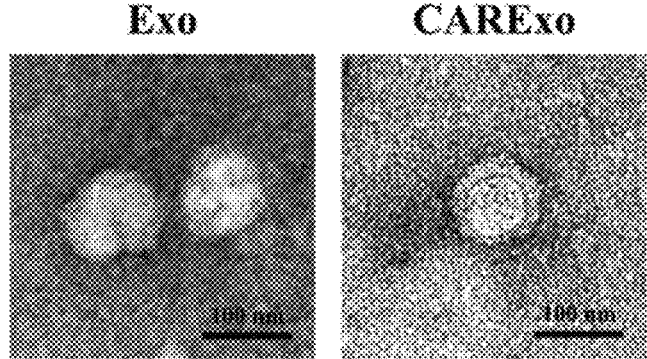
FIGS. 1A-1B show the verification of morphology and size of exosome with/without cargo engineering.

This present invention establishes a high-quality and mass-production engineering modified exosome platform by adjusting the parental cell culture parameters. Via a 3D dynamical stimulation process, parental cell (HEK 293) secretes a large amount of high purity exosomes as a biological product. Three platforms are framed in this present invention, including genetic modified membrane targeting HLA-G, an exosome mass-production system, combined drugs loaded design. The present invention is capable of achieving several outcomes: 1) the amount of exosome secreted from 1HEK293 under dynamic culture environment can produce 45-300 times of exosomes with high expression of CD63, which provides the high quality and quantity of exosomes for treatment; 2) High efficiency of killing cancer cells without side-effect due to low chemo drug loading; 3) CARExos carry anti-HLA-G protein and miRNA 34a, which leads to repress tumor progression and will slow down the process of tumor metastasis; 4) CAR-Exos show outstanding tumor size control and no metastasis in animal model. The present invention believes that CAR-Exos own high potential to be an efficient anti-cancer weapon for patients in the future, with huge potential and business opportunities.

The terms "a" or "an" as used herein describe the elements and components of the present invention. This term is used only for convenience of description and to give a basic idea of the present invention. This description should be understood to include one or at least one, and unless it is clear that it is indicated otherwise, the singular also includes the plural. When used in conjunction with the word "comprising" in a claim, the term "a" may mean one or more than one.

The term "or" as used herein in a claim means "and/or," unless expressly indicated to mean only the other option, or unless the other options are mutually exclusive.

The present invention provides a method for promoting production of exosomes, which comprises: (a) providing a cyclic tensile bioreactor, wherein the cyclic tensile bioreactor comprises a culture chamber, a biocompatible polymeric material with an auxetic structure and a plurality of tensile components, the biocompatible polymeric material and the plurality of tensile components are placed in the culture chamber, the biocompatible polymeric material comprises exosome-producing cells, and two ends of the biocompatible polymeric material are connected with the plurality of tensile components; (b) repeatedly stretching the biocompatible polymeric material by the plurality of tensile components to apply cyclic tensile force; and (c) collecting the exosomes which are released from the exosome-producing cells by the cyclic tensile force applied by the plurality of tensile components.

In one embodiment, the biocompatible polymeric material comprises a methacryloyl-based polymer. In a preferred embodiment, the methacryloyl-based polymer comprises gelatin methacryloyl (GelMa), collagen methacryloyl, hyaluronic acid methacryloyl (HAMa), chondroitin sulfate methacryloyl, chitosan methacryloyl, alginate methacryloyl, or decellularized extracellular matrix with methacryloyl (dECMMa). In a more preferred embodiment, the gelatin methacryloyl comprises fish gelatin methacryloyl (FGelMa) or porcine gelatin methacryloyl (PGelMa). Furthermore, the gelatin methacrylamide is prepared by a gelatin from fish or porcine, methacrylic anhydride and a solution (e.g. phosphate buffer solution). Thus, the methacrylamide-based polymer is biodegradable and biocompatible.

In the present invention, the concentration of the biocompatible polymeric material affects the auxetic function of the biocompatible polymeric material, and the the auxetic function further affects the production of the exosomes. Therefore, the present invention uses the biocompatible polymeric material with different concentrations for affecting the yield of exosomes. For example, the concentration of GelMa ranges from 5 wt % to 30 wt %, the concentration of alginate methacryloyl ranges from 1 wt % to 10 wt %, the concentration of collagen methacryloyl ranges from 0.5 wt % to 10 wt %, the concentration of HAMa ranges from 1 wt % to 10 wt %, and the concentration of dECMMa ranges from 1 wt % to 10 wt %. In one embodiment, the concentration of the biocompatible polymeric material ranges from 0.1 wt % to 50 wt %. In a preferred embodiment, the concentration of the biocompatible polymeric material ranges from 0.2 wt % to 40 wt %. In a more preferred embodiment, the concentration of the biocompatible polymeric material ranges from 0.5 wt % to 30 wt %.

In the present invention, the concentration of the biocompatible polymeric material is adjusted by dilution. For example, if the biocompatible polymeric material is FGelMa, a 20 wt % of FGelMa is prepared by mixing 20 g of FGelMa with 80 g of distilled water.

In addition, the biocompatible polymeric material with the auxetic structure is able to withstand at least 5% of tensile strain applied by the tensile components without being torn. In one embodiment, the mechanical strength of the biocompatible polymeric material with the auxetic structure withstands 2.5-50% of tensile strain. In a preferred embodiment, the mechanical strength of the biocompatible polymeric material with the auxetic structure withstands 5-40% of tensile strain. In a more preferred embodiment, the mechanical strength of the biocompatible polymeric material with the auxetic structure withstands 10-30% of tensile strain.

In some aspects, the term "tensile strain" is defined as the deformation or elongation of a solid body due to the application of a tensile force or stress. In other words, tensile strain is produced when a body increases in length as applied forces try to stretch it. Tensile strain can be expressed mathematically by the formula: $\varepsilon=\Delta L/L$, wherein $\varepsilon=$Tensile strain, $\Delta L=$Change in length, and L=Original length.

In the present invention, the biocompatible polymeric material is designed to be shaped like a dumb-bell with two ends being wider than the body. Therefore, the biocompatible polymeric material is able to be divided into two parts: one part is a first polymeric material with an auxetic structure, and the other part comprises two second polymeric materials with rigid structure. Therefore, the mechanical strength of each second polymeric material with the rigid structure is higher than that of the first polymeric material with the auxetic structure. These two second polymeric materials are connected to two ends of the first polymeric material, respectively. The cells are loaded into the auxetic structure of the first polymeric material. Therefore, the first polymeric material is used for loading the cells, and the second polymeric materials are used for providing appropriate connections between the first polymeric material and the plurality of tensile components.

In one embodiment, the biocompatible polymeric material comprises a first polymeric material and two second polymeric materials. In a preferred embodiment, the two second polymeric materials are connected to two ends of the first polymeric material, respectively. In a more preferred embodiment, the first polymeric material is used for loading the exosome-producing cells, and the second polymeric material is used for connecting the first polymeric material and the plurality of tensile components. In another embodiment, the first polymeric material is FGelMa, and the second polymeric material is GelMa.

The exosome-producing cells are able to be loaded into the biocompatible polymeric material or the first polymeric material by known methods. After the exosome-producing cells are loaded into the biocompatible polymeric material with the auxetic structure, the present invention can obtain a cell-laden auxetic scaffold. In the present invention, the biocompatible polymeric material is a cell-laden FgelMa, and the cell-laden FgelMa is obtained by mixing the exosome-producing cells with FGelMa.

The exosome-producing cells may be present in the form of e.g. primary cells, cell lines, cells present in a multicellular organism, or essentially any other type of cell source and exosome-producing cell material. The term "exosome-producing cell" may be understood to relate to any type of cell that is capable of producing exosomes under suitable conditions, for instance in a suspension culture or in an adherent culture or in any other type of culture system. The exosome-producing cells may also include cells producing exosomes in vivo. The exosome-producing cells may be selected from a wide range of cells and cell lines which may grow in a suspension culture or an adherent culture or being adapted to suspension growth. The exosome-producing cells may be selected from the group comprising: mesenchymal stem or stromal cells (obtainable from e.g. bone marrow, adipose tissue, Wharton's jelly, perinatal tissue, placenta, tooth buds, umbilical cord blood, skin tissue, etc.), fibroblasts, amnion cells and more specifically amnion epithelial cells optionally expressing various early markers, myeloid suppressor cells, M2 polarized macrophages, adipocytes, and endothelial cells etc. Cell lines of particular interest include human umbilical cord endothelial cells (HUVECs), human embryonic kidney (HEK) cells, endothelial cell lines such as microvascular or lymphatic endothelial cells, erythrocytes, erythroid progenitors, chondrocytes, mesenchymal stem cells (MSCs) of different origin, amnion cells, amnion epithelial (AE) cells, any cells obtained through amniocentesis or from the placenta, epithelial cells from the airways or alveolae, fibroblasts, endothelial cells, etc. Also, immune cells such as B cells, T cells, NK cells, macrophages, monocytes, dendritic cells (DCs) are also within the scope of the present invention, and essentially any type of cell which is capable of producing exosomes is also encompassed herein. Generally, exosomes may be derived from essentially any cell source, a primary cell source or an immortalized cell line. Cell lines of particular interest include human umbilical cord endothelial cells (HUVECs), human embryonic kidney (HEK) cells such as HEK293 cells, HEK293T cells, serum free HEK293 cells, suspension HEK293 cells, endothelial cell lines such as microvascular or lymphatic endothelial cells, erythrocytes, erythroid progenitors, chondrocytes, MSCs of different origin, amnion cells, amnion epithelial (AE) cells, any cells obtained through amniocentesis or from the placenta, airway or alveolar epithelial cells, fibroblasts, endothelial cells, epithelial cells, etc. In one embodiment, the exosome-producing cells comprises mammalian cells. In a preferred embodiment, the exosome-producing cells comprises embryonic kidney cells. In a more preferred embodiment, the exosome-producing cells comprises HEK293 cells. Therefore, the exosome-producing cells is able to produce exosomes that retain the biological property of exosomes, and the exosomes may have the expression of CD9, CD63, CD81 and HSP70.

In the present invention, there are a plurality of pores in the biocompatible polymeric material or the first polymeric material. The plurality of pores are designed to increase the auxetic functions of the auxetic structure in the biocompatible polymeric material or the first polymeric material. In addition, the plurality of pores can make the culture solution to flow into the biocompatible polymeric material or the first polymeric material for cell culture. In one embodiment, the biocompatible polymeric material or the first polymeric material comprises a plurality of pores. In addition, the the plurality of pores have various types according to the auxetic need. In one embodiment, the shape of a pore comprises a sphere shape, an ellipsoid shape, a rhombogene shape, or a spindle-like shape. In a preferred embodiment, the shape of the pore is the spindle-like shape. In another embodiment, the spindle-like shape of the pore is designed with 1 to 5 mm in length and 0.1 to 0.5 mm wide. In a preferred embodiment, the the spindle-like shape of the pore is designed with 2 to 4 mm in length and 0.2 to 0.4 mm wide. Furthermore, the plurality of pores are designed to pierce through the structure of the biocompatible polymeric material or the first polymeric material.

In some embodiments, the culture chamber is filled with a culture solution, and the biocompatible polymeric material is placed in the culture solution. In one embodiment, the culture chamber contains a culture solution.

In various embodiments, the cyclic tensile force is applied by the plurality of tensile components. The biocompatible polymeric material with the auxetic structure is strained by the cyclic tensile force of the plurality of tensile components. In one embodiment, the cyclic tensile force applied by the plurality of tensile components is at a tensile strain of 2.5-50%. In a preferred embodiment, the cyclic tensile force applied by the plurality of tensile components is at a tensile strain of 5-40%. In a more preferred embodiment, the cyclic tensile force applied by the plurality of tensile components is at a tensile strain of 10-30%. In another embodiment, the cyclic tensile force applied by the plurality of tensile components is at a frequency of 0.1-4 Hz. In a preferred embodiment, the cyclic tensile force applied by the plurality of tensile components is at a frequency of 0.2-2 Hz. In a more preferred embodiment, the cyclic tensile force applied by the plurality of tensile components is at a frequency of 0.3-1 Hz. In one embodiment, the plurality of tensile components the provide cyclic uniaxial tensile force on the biocompatible polymeric material. In another embodiment, the cyclic tensile force of the plurality of tensile components is applied at a horizontal direction along with the biocompatible polymeric material. Therefore, the biocompatible polymeric material containing the exosome-producing cells is treated with a cyclic tensile force for stimulating the cells to release exosomes.

In the present invention, the biocompatible polymeric material is treated with the cyclic tensile force for more than one week, and then the exosomes are collected from the exosome-producing cells in the biocompatible polymeric material. In one embodiment, the collecting of the exosomes in the step (c) is made about one week, about two weeks, about three weeks, about one month, about two months, or about three months after the cyclic tensile force is applied. In a preferred embodiment, the collecting of the exosomes in the step (c) is made about one to two months after the cyclic tensile force is applied. In another embodiment, the number of the exosomes collected one month after the cyclic force is applied is between $0.1 \times 10^6$ to $2 \times 10^6$/per cell. In a preferred embodiment, the number of the exosomes collected one month after the cyclic force is applied is between $0.5 \times 10^6$ to $1.5 \times 10^6$/per cell.

When the cyclic tensile force is applied to the cells, the cells change from single cells to self-assembled three-dimensional (3D) cell spheroids and express a large amount of Yes-associated protein (YAP). The present invention demonstrates that the cyclic tensile force can stimulate the cells to express a large amount of YAP protein, and the YAP protein is able to make the cells form the 3D spheroids, resulting in a significant increase in the secretion of exosomes. In one embodiment, the form of the exosome-producing cells changes into a 3D cell spheroid under the cyclic tensile force. In another embodiment, the exosome-producing cells express a large amount of YAP protein under the cyclic tensile force. Thus, the 3D cell culture method using the cyclic tensile bioreactor of the present invention can produce exosomes at a large scale.

The present invention provides a polynucleotide, which comprises a sequence encoding a fusion protein, wherein the fusion protein comprises a targeting protein and an exosomal transmembrane protein, and the targeting protein comprises an anti-human leukocyte antigen G (HLA-G) protein.

Furthermore, the sequence encoding the fusion protein is a nucleic acid sequence. In some aspects, the sequence encoding the fusion protein comprises a first sequence encoding the targeting protein and a second sequence encoding the exosomal transmembrane protein. In one embodiment, the sequence encoding the fusion protein comprises SEQ ID NO: 1. In a preferred embodiment, the first sequence encoding the anti-HLA-G protein (the targeting protein) comprises SEQ ID NO: 1.

In the present invention, the exosomal transmembrane protein is a transmembrane or a membrane-associated protein. In another embodiment, the exosomal transmembrane protein is a transmembrane domain of CD9, CD53, CD63, CD81, CD82, CD54, CD50, FLOT1, FLOT2, CD49d, CD71, CD133, CD138, CD235a, ALIX, Syntenin-1, Syntenin-2, Lamp2b, TSPAN8, syndecan-1, syndecan-2, syndecan-3, syndecan-4, TSPAN14, CD37, CD82, CD151, CD231, CD102, NOTCH1, NOTCH2, NOTCH3, NOTCH4, DLL1, DLL4, JAG1, JAG2, CD49d/ITGA4, ITGB5, ITGB6, ITGB7, CD11a, CD11b, CD11c, CD18/ITGB2, CD41, CD49b, CD49c, CD49e, CD51, CD61, CD104, Fe receptors, interleukin receptors, immunoglobulins, MHC-I, MHC-II, CD2, CD3 epsilon, CD3 zeta, CD13, CD18, CD19, CD30, CD34, CD36, CD40, CD40L, CD44, CD45, CD45RA, CD47, CD86, CD110, CD111, CD115, CD117, CD125, CD135, CD184, CD200, CD279, CD273, CD274, CD362, COL6A1, AGRN, EGFR, GAPDH, GLUR2, GLUR3, HLA-DM, HSPG2, LICAM, LAMBI, LAMC1, ARRDC1, LFA-1, LGALS3BP, Mac-1 alpha, Mac-1 beta, MFGE8, SLIT2, STX3, TCRA, TCRB, TCRD, TCRG, VTI1A, VTI1B, or combination thereof. In a preferred embodiment, the exosomal transmembrane protein is a transmembrane domain of CD9, CD63 or CD81. In a more preferred embodiment, the exosomal transmembrane protein is a transmembrane domain of CD63.

In the present invention, the polynucleotide further comprises a promoter, which is operably linked to the sequence encoding the fusion protein. As used herein, "promoter" means a synthetic or naturally derived molecule capable of conferring, activating or enhancing the expression of a nucleic acid in a cell. A promoter may comprise one or more specific transcriptional regulatory sequences to further enhance expression and/or alter its spatial expression and/or temporal expression. In some embodiments, the promoter can drive and be linked to the upstream of the sequence encoding the fusion protein. The promoters that can be linked are not particularly limited, as long as they show promoter activity in the target cell. Examples of the promoters that can be linked to the sequence encoding the fusion protein comprises, but are not limited to, an EFS promoter, a cytomegalovirus (CMV) promoter, a CK8 promoter, a MHC promoter, a MYOD promoter, an hTERT promoter, a SRalpha promoter, a SV40 promoter, a LTR promoter, a CAG promoter, a Rous sarcoma virus (RSV) promoter and the like. In one embodiment, the polynucleotide further comprises a promoter, which is used for regulating the sequence encoding the fusion protein.

Further, the present invention further provides a vector, wherein the vector carries the polynucleotide. Therefore, the polynucleotide having the sequence encoding the fusion protein is in the vector. In the present invention, one or more vectors are used, which respectively carry different sequence fragments.

In one embodiment, the vector is a plasmid vector, a non-viral vector or a viral vector. When the vector of the present invention is a plasmid vector, the plasmid vector to be used is not particularly limited and can be any plasmid vectors (such as cloning plasmid vectors and expression plasmid vectors). The plasmid vector comprising the polynucleotide of the present invention is prepared by inserting the polynucleotide of the present invention into a plasmid vector by known methods. In a preferred embodiment, the viral vector comprises an adenovirus vector, an adeno-associated virus (AAV) vector, a lentiviral vector, a retrovirus or Sendaivirus vector. In the instant specification, "viral vector" also includes derivatives thereof. The viral vector comprising the polynucleotide of the present invention can be prepared by known methods. In another embodiment, the non-viral vector comprises a liposome or a lipid nanoparticle.

In some aspects, the exosome-producing cells are transfected with a vector carrying the polynucleotide. Therefore, the exosome-producing cells normally comprise the polynucleotide encoding the fusion protein. Thus, the successfully transfected cells can produce a single, double or multiply stable cell lines. Single stable cell lines are advantageous because the production of exosomes is simplified by requiring only the transfection of a single polynucleotide.

Preferably the exosome-producing cells are stably transfected with the polynucleotide encoding the fusion protein, such that a stable cell line is generated. This advantage results in consistent production of exosomes of uniform quality and yield. The exosome-producing cells may be genetically modified with at least one polynucleotide using essentially any non-viral or viral method for introducing a polynucleotide into a cell. Suitable methods for introducing the polynucleotide into an exosome-producing cell include transfection using polycations such as PEI, lipid-based transfection reagents such as Lipofectamine®, lentiviral transduction, CRISPR-Cas guided insertion, Flp-In system, transposon system, electroporation, DEAE-Dextran transfection, and calcium phosphate transfection. The choice of method for introducing the polynucleotide into an exosome-producing cell depends on various parameters, including choices of cell source, the nature and characteristics of the vector (e.g. if the vector is a plasmid or a minicircle, e.g. a linear DNA polynucleotide or an mRNA), and the level of compliance and control needed. Similarly, immortalization of exosome-producing cells to create stable cell lines can be achieved by using techniques that are well known in the art of cell line development, including hTERT-mediated immortalization, transcription factor immortalization, E1/E2 immortalization or other virus-mediated immortalization techniques, etc. Thus, the successfully transfected exosome-producing cells can release the exosomes having the fusion protein.

In an additional aspect, the present invention provides a method for producing an exosome comprising a fusion protein, which comprises: (1) introducing a polynucleotide into an exosome-producing cell, wherein the polynucleotide comprises a sequence encoding a fusion protein, the fusion protein comprises a targeting protein and an exosomal transmembrane protein, and the targeting protein comprises an anti-human leukocyte antigen G (HLA-G) protein; and (2) allowing the exosome-producing cell to produce the exosome comprising the fusion protein.

In one embodiment, the exosome-producing cells comprise mammalian cells. In a preferred embodiment, the exosome-producing cells comprise embryonic kidney cells. In a more preferred embodiment, the exosome-producing cells comprise HEK293 cells.

The present invention provides a fusion protein, which comprises a targeting protein and an exosomal transmembrane protein, wherein the targeting protein comprises an anti-HLA-G protein, and the sequence of the anti-HLA-G protein comprises SEQ ID NO: 2. The peptide sequence of SEQ ID NO: 2 is generated by the nucleic acid sequence of SEQ ID NO: 1.

The present invention further provides a cell, which comprises a fusion protein, wherein the fusion protein comprises a targeting protein and an exosomal transmembrane protein, the targeting protein comprises an anti-HLA-G protein, and the sequence of the anti-HLA-G protein comprises SEQ ID NO: 2. In one embodiment, the cell is an exosome-producing cell.

In some aspects, the targeting protein directly connects with the exosomal transmembrane protein to form the fusion protein. The use of an exosomal transmembrane protein makes it possible to configure the targeting protein on the outside of the exosomal membrane. This configuration supports exposing the targeting protein to the outside to enable binding to molecules on tissues. Suitable exosomal transmembrane protein may be selected from the group comprising CD63, CD81, CD9, CD82, CD44, CD47, CD55, LAMP2B, ICAMs, integrins, ARRDC1, annexin, and any other exosomal polypeptides, and any combinations, derivatives, domains, or regions thereof. A non-limiting example could be a protein such as CD63.

The present invention also provides an exosome, which comprises a fusion protein, wherein the fusion protein comprises a targeting protein and an exosomal transmembrane protein, the targeting protein comprises an anti-HLA-G protein, and the sequence of the anti-HLA-G protein comprises SEQ ID NO: 2. In one embodiment, the exosomal transmembrane protein comprises CD9, CD63 or CD81. In a preferred embodiment, the exosomal transmembrane protein comprises CD63.

In one embodiment, the exosome further comprises a therapeutic agent. In a preferred embodiment, the therapeutic agent comprising antibodies, antibody fragments, antibody derivatives, single domain antibodies, intrabodies, single chain variable fragments, affibodies, enzymes, transporters, tumor suppressors, viral or bacterial inhibitors, cell component proteins, DNA and/or RNA binding proteins, DNA repair inhibitors, nucleases, proteinases, integrases, transcription factors, growth factors, apoptosis inhibitors and inducers, toxins, structural proteins, neurotrophic factors, membrane transporters, nucleotide binding proteins, heat shock proteins, CRISPR-associated proteins, and a combination thereof. The therapeutic agent is able to be loaded into the exosome. Hence, a therapeutic exosome is obtained by introducing/loading the therapeutic agent into the exosome which comprises the fusion protein.

In one embodiment, the therapeutic agent comprises an anti-cancer agent. In a preferred embodiment, the anti-cancer agent comprises a chemotherapy agent. In a more preferred embodiment, the anti-cancer agent comprises a microRNA (miR) for treating cancer.

In another embodiment, the chemotherapy agent comprises remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, herceptin, perjeta, epirubicin, pemetrexed, thiotepa, fludarabine, liposomal daunorubicin, cytarabine, pacilitaxel, vinblastine, IL-2, GM-CSF, dacarbazine, vinorelbine, zoledronic acid, palmitronate, biaxin, busulphan, prednisone, bortezomib (Velcade®), bisphosphonate, arsenic trioxide, doxorubicin (Doxil®), ganciclovir, adriamycin, estrainustine sodium phosphate (Emcyt®), sulindac, etoposide, or a combination thereof. In a preferred embodiment, the chemotherapy agent comprises doxorubicin (DOX), taxotere (Taxo), cisplatin (Cisp), herceptin, perjeta, epirubicin (Epir), cyclophosphamide (Cycl), carboplatin (Carb), gemcitabine (Gemc), pemetrexed (Peme), or a combination thereof. In a more preferred embodiment, the chemotherapy agent comprises doxorubicin.

In another embodiment, the microRNA for treating cancer comprises miR-34a, miR-34b, miR-34c, miR-497, miR-145, miR-206, miR-21, miR-99a, miR-30a, miR-30a, miR-9, miR-210, miR-192, miR-494, miR-221, miR-19a, miR-19b, miR-23b-3p, miR-122-5p, miR-193b-3p, miR-141, miR-375, miR-145, miR-196a-5p, miR-200c-3p, miR-1246, miR-1290, miR-21-5p, miR-127-3p, miR-200a, miR-200b, miR-200c, miR-339-5p or miR-409-3p. In another embodiment, the microRNA for treating cancer comprises miR-34a.

The present invention provides a composition, which comprises an exosome comprising a fusion protein, wherein the fusion protein comprises a targeting protein and an exosomal transmembrane protein, the targeting protein comprises an anti-HLA-G protein, and the sequence of the anti-HLA-G protein comprises SEQ ID NO: 2.

The present invention provide a method for treating a subject with cancer, comprising administering a composition into the subject with cancer, wherein the composition comprises a therapeutic exosome, and the therapeutic exosome comprises a fusion protein and an anti-cancer agent, and the fusion protein comprises a targeting protein and an exosomal transmembrane protein, the targeting protein comprises an anti-HLA-G protein, and the sequence of the anti-HILA-G protein comprises SEQ ID NO: 2. In one embodiment, the exosomal transmembrane protein comprises CD9, CD63 or CD81. In a preferred embodiment, the exosomal transmembrane protein comprises CD63.

The present invention further provides a use of a composition for preparing a drug for treating cancer, wherein the composition comprises a therapeutic exosome, the therapeutic exosome comprises a fusion protein and an anti-cancer agent, the fusion protein comprises a targeting protein and an exosomal transmembrane protein, the targeting protein comprises an anti-HILA-G protein, and the sequence of the anti-HLA-G protein comprises SEQ ID NO: 2. In one embodiment, the exosomal transmembrane protein comprises CD9, CD63 or CD81. In a preferred embodiment, the exosomal transmembrane protein comprises CD63.

The term "treating" encompasses, but is not limited to, reducing, inhibiting or limiting the growth of cancer cells, reducing, inhibiting or limiting metastasis of the cancer cells or invasiveness of the cancer cells or metastasis or reducing, inhibiting or limiting one or more symptoms of the cancer or metastasis thereof. As used herein, the "inhibiting growth of cancer cells" refers to any slowing of the rate of cancer cell proliferation and/or migration, arrest of cancer cell proliferation and/or migration, killing of cancer cells, or reducing cell viability, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, deter the growth, and reduce the presence of a tumor.

The terms "cancer" or "tumor" as used herein refer to or describe the physiological condition in mammals in which a population of cells are characterized by unregulated cell growth. A cancer may be a non-solid tumor or a solid tumor. Examples of cancer include, but are not limited to, carcinoma, lymphoma, blastoma, sarcoma, and leukemia. More particular examples of such cancer include breast cancer, oral cancer, medulloblastoma, prostate cancer, squamous cell cancer, lung cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, ovarian adenocarcinoma, liver cancer, bladder cancer, hepatoma, colon cancer, colorectal cancer, gastric cancer, endometrial or uterine carcinoma, salivary gland carcinoma, kidney cancer, liver cancer, vulvar carcinoma, thyroid cancer, hepatic carcinoma and various types of head and neck cancer, hematologic malignancies, acute myeloid leukemia, lymphoma and leukemia, and melanoma, among others. In one embodiment, the cancer comprises breast cancer, lung cancer, oral cancer, liver cancer, colorectal cancer, glioblastoma, medulloblastoma, bladder cancer, pancreatic cancer, or ovarian cancer. In a preferred embodiment, the cancer comprises breast cancer.

In one embodiment, the subject is an animal, preferably a mammal, more preferably a human.

In another embodiment, the anti-cancer agent comprises a chemotherapy agent and/or a microRNA (miR) for treating cancer. In a preferred embodiment, the chemotherapy agent comprises doxorubicin (DOX), taxotere (Taxo), cisplatin (Cisp), herceptin, perjeta, epirubicin (Epir), cyclophosphamide (Cycl), carboplatin (Carb), gemcitabine (Geme), or pemetrexed (Peme), or a combination thereof. In a more preferred embodiment, the chemotherapy agent comprises doxorubicin. In another embodiment, the microRNA for treating cancer comprises miR-34a.

In the present invention, the anti-HLA-G protein is a protein or a peptide having an anti-HLA-G function. Therefore, the anti-HLA-G protein is able to specifically bind to HLA-G molecule. In particular, the sequence of SEQ ID No: 2 in the present invention present a higher affinity for HLA-G. In some aspects, HLA-G molecules are expressed on cancer cells. Hence, the exosomes having anti-HLA-G proteins can specifically bind to the cancer cells, and are used as as drug delivery tools in the treatment of cancer.

In some embodiments, the therapeutic exosome is administered with a pharmaceutically acceptable carrier. The term "pharmaceutically acceptable carrier" refers any carrier, diluent or excipient that is compatible with the other ingredients of the formulation and not deleterious to the recipient. A pharmaceutically acceptable carrier can be selected on the basis of the selected route of administration and standard pharmaceutical practice. The therapeutic exosome may be formulated into dosage forms according to standard practices in the field of pharmaceutical preparations. Suitable dosage forms comprise, but are not limited to, for example, solutions, parenteral solutions, injectable solutions, troches, suppositories, or suspensions.

The composition of the present invention comprising the therapeutic exosome can be administered to the subject by various routes, including oral, parenteral, sublingual, transdermal, rectal, transmucosal, topical, via inhalation, via buccal administration, intrapleural, intravenous, intraarterial, intraperitoneal, subcutaneous, intramuscular, intranasal, intrathecal, and intraarticular, or a combination thereof. In a preferred embodiment, the composition is administered by intravenous or parenteral administration. In another embodiment, the composition is administered by direct injection into the tumor.

For parenteral administration, the active agent may be mixed with a suitable carrier or diluent such as, but not limited to, water, an oil (e.g., a vegetable oil), ethanol, saline solution (e, g., phosphate buffer saline or saline), aqueous dextrose (glucose) and related sugar solutions, glycerol, or a glycol such as propylene glycol or polyethylene glycol. Stabilizing agents, antioxidant agents and preservatives may also be added. Suitable antioxidant agents include, but are not limited to, sulfite, ascorbic acid, citric acid and its salts, and sodium EDTA. Suitable preservatives include, but are not limited to, benzalkonium chloride, methyl- or propyl-paraben, and chlorbutanol. The composition for parenteral administration may take the form of an aqueous or nonaqueous solution, dispersion, suspension or emulsion.

According to the present invention, the dosage of the composition comprising the therapeutic exosome is not particularly limited, as long as it is an effective amount for treatment. It can be appropriately optimized according to active ingredients, dosage form, age and body weight of the subject, administration schedule, administration method, and the like. The composition is preferably in unit dosage form. In such form the preparation is divided into unit doses containing appropriate quantities of the active component.

The method for treating cancers comprises administering a therapeutically effective amount of the therapeutic exosome in order to reduce, inhibit or limit the growth of the cancer. The term "therapeutically effective amount" refers to an amount sufficient to effect beneficial or desirable biological and/or clinical results. In one embodiment, the "therapeutically effective amount" is an amount sufficient to inhibit, reduce or limit the growth of cancer cells as compared with the observed or predicted rate of growth of an untreated control cancer.

Dosage amounts of the anti-cancer agent, miR or the therapeutic exosome is typically in the range of from about 0.0001 or 0.001 or 0.01 mg/kg/day to about 1000 mg/kg/day, but can be higher or lower, depending upon, among other factors, the activity of the composition, its bioavailability, the mode of administration, and various factors discussed above. The dosage amount and interval can be adjusted individually to provide local and/or systemic concentration of the exosomes that are sufficient to maintain therapeutic or prophylactic effect. For example, the composition can be administered once per week, several times per week (e.g., every other day), once per day, or multiple times per day, depending upon, among other things, the mode of administration, the specific indication being treated, and the judgment of the prescribing physician. Skilled artisans will be able to optimize effective local dosages without undue experimentation. In one embodiment, the therapeutically effective amount of the chemotherapy agent ranges from 0.01 to 10 mg/kg weight. In another embodiment, the therapeutically effective amount of the microRNA for treating cancer ranges from 0.01 to 1 mg/kg weight.

In addition, in the present invention, the exosome-producing cells comprising the fusion protein can be applied in the cyclic tensile bioreactor of the present invention. The exosomses are advantageous as delivery vehicles due to a variety of benefits such as lack of immunogenicity and ability to efficiently home to different organs. Therefore, the culture method using the cyclic tensile bioreactor of the present invention are suitable for consistent and large scale production of exosomes that retain the biological property of exosomes and contain the fusion protein, making these exosomes suitable as delivery tools for agents (e.g. therapeutic agents).

Examples

The present invention may be embodied in many different forms and should not be construed as limited to the examples set forth herein. The described examples are not intended to limit the scope of the invention as set forth in the claims.

Materials and Methods

Vector Construction and Cell Line Establishment

Sequence encoding anti-HLA-G VHH/VCD63-fusion protein was synthesized and inserted into pcDNA3.4 plasmid (Thermo Scientific) in series by molecular cloning technique to create an anti-HILA-G-CD63 expressing plasmid (as pcDNA3.4-αHLA-G-CD63). The DNA sequence of the insert was validated by the Sanger sequencing method. For establishing a stable expression cell line, 293T cells were transfected with the pcDNA3.4-αHLA-G-CD63 by using Lipofectamine 3000 reagent (Thermo Scientific). After transfection, stably transfected 293T cells were selected by culture in G418 (800 μg/mL, Invivogen). 293T cells could produce exosome having anti-HILA-G/CD63-fusion protein as a cargo exosome (CAExo).

The nucleic acid sequence encoding anti-HLA-G protein is:

(SEQ ID No: 1)
AGCGCTGGTCACGTGCAGCTGGTGGAAAGCGGCGGCGGCAGCGTGC

AAGCCGGCGGCAGCCTGAAGCTGAGCTGCGTGACAAGCGCCTACAC

CTTCTCCGCTAGCGGCAACTGCATGGGCTGGCTGAGACAAGCCCCCG

GCAAGGGCAGAGAGGGCATCGCCGCCACCTACACAAGAAGCGCCAA

GACCTACTACGCCGACAGCGTGAAGGGCAGATTCACCATCAGCCAAG

ACAACGCCAAGAACACCGTGTACCTGCAGATGAACGGCCTGAAGCCC

GAGGACACCGCCACCTACTACTGCGCCGTGGCTAGATGCGCCGGCAG

ACCCGACAGAAGCACCCTGACAAGCTTCGCCTGGTGGGGCCAAGGC

ACCCAAGTGACCGTGAGCAGCCTGGAGACCGGT.

The peptide sequence of anti-HLA-G protein is:

(SEQ ID No: 2)
SAGHVQLVESGGGSVQAGGSLKLSCVTSAYTFSASGNCMGWLRQAPGKGR

EGIAATYTRSAKTYYADSVKGRFTISQDNAKNTVYLQMNGLKPEDTATYY

CAVARCAGRPDRSTLTSFAWWGQGTQVTVSSLETG.

Fabrication and Characterization of Exo and CAExo

To obtain the exosomes (Exo or CAExo), the medium was centrifuged at 2000 g for 15 min to remove cellular debris and filtered with 0.22 μm filter paper. Then, the supernatant was concentrated by ultrafiltration (Amicon® Ultra, 30 kDa, Merck Millipore, Billerica, MA, USA) at 5000 g for 8 min. The collected supernatant was used tangential flow filtration (MAP.03-plus TFF System, Lefo Science, Taipei, Taiwan), and sequentially filtered through membranes with 300 kDa molecular weight cut off and resuspended by phosphate buffer solution (PBS) (pH=7.4), which were detailed above. All samples were operated at 4° C. to immediately use or stored at −80° C. for further use. After isolation, the Exo/CAExo were fixed with 1% glutaraldehyde at 4° C. overnight. After washing, Exo/CAExo were loaded onto formvar carbon-coated grids, negatively stained with aqueous phosphotungstic acid for 1 min. The ultrastructure of Exo/CAExo was analyzed by transmission electron microscopy (TEM, JEOL JEM-1400, Tokyo, Japan).

These Exo were also assayed by nanoparticle tracking analysis (NTA, ZetaView®, Particle Metrix GmbH, Meerbusch, Germany) to analyze the size distribution and concentration of exosomes. To analyze the biomarkers, Exo/CARExo were immersed and gently mixed with magnetic capture beads coated with anti-CD9 antibody (ab239685, Abcam), anti-CD63 antibody (ab239686, Abcam) and anti-CD81 antibody (ab239687, Abcam) at room temperature for 12 h. The pre-bound Exo/CARExo were washed and placed on a DynaMag™ (Invitrogen) for 10 min before the supernatant was discarded. The bead-bound Exo/CARExo were re-suspended in buffer and incubated with PE anti-CD9 antibody (E-AB-F1086D, Elabscience, Houston, TX, USA), or PE anti-CD63 antibody (ab205540, Abcam), or anti-CD81 antibody (E-AB-F1073D, Elabscience) at 4° C. for 2 h. The PE (phycoerythrin)-labeled bead-bound Exo were analyzed using BD Accuri™ C6 Plus flow cytometry (BD FACS, San Jose, CA, USA). In addition, western blotting was used to determine specific Exo/CARExo biomarkers such as CD63, CD81, HSP70, Alix, and β-tubulin (Abcam).

Exo Uptake Assay

PKH26-labeled Exo/CARExo were mixed in 2 mL MDA-MB-231 and MCF10A medium ($10^{1}$ Exo/mL). First, these two cell lines were grown to 60% confluence in p-slide well (ibidi GmbH, Grafelfing, Germany), and then the medium was changed with medium containing PKH26-labeled Exo. After being cultured for 6, 12, and 24 h, the cells were washed twice with PBS, fixed, and stained with Alexa Fluor™ 488 Phalloidin and DAPI. After washing, the images of the cells were captured using the fluorescence microscope (BX53, Olympus, Tokyo, Japan).

Cell Viability

The cell cultured on 96-well with Exo/CARExo for the collection of different time-points, the culture medium was collected and washed with PBS solution to remove any residual medium. Tetrazolium dye MTT (3-(4,5-dimethyl-thiazol-2-yl)-2,5-diphenyltetrazolium bromide) (Sigma-Aldrich) was mixed fresh medium with ratio of 1:9 and performed to assess for cell viability, which worked by acting on the respiratory chain. After 3 h of reaction, the MTT agent was removed and DMSO was added and left aside for 20 min to dissolve the formazan crystals and redistributed evenly into a 96-well. Absorbance was quantified by measuring at a wavelength of 570 nm to assess for cell viability.

Immunofluorescence

MDA-MB-231, MCF-7 and MCF-10A cells (at a density of $5\times10^{4}$ cells/mL) were seeded onto 35-mm dish with cover slips and were allowed to adhere for 12 h. MDA-MB-231, MCF-7 and MCF-10A cells were cultured in the presence of either nanoprobe (0 and 5 μM) at 37° C. for 6 h. Cells were washed once in PBS, fixed, and permeabilized simultaneously using 4% paraformaldehyde with 1% Triton X-100 in PBS. They were then quenched with 0.1 M glycine in PBS, and blocked overnight at 4° C. with 3% (wt/vol) BSA. The fixed and permeabilized cells were stained with primary and secondary antibodies as has been prescribed. Then, cells were stained by DAPI solution at room temperature for 5 min. Goat Anti-Mouse IgG H&L (Alexa Fluor®647) (ab150115) and Goat Anti-Rabbit IgG H&L (Alexa Fluor®488) (ab150077) were obtained from Abcam (Cambridge, UK). Cell morphology was observed using a laser confocal microscope (Zessis, LSM800, Germany).

Preparation of miRNA and Doxorubicin (DOX)-Load Exo/CARExo

To load Exo/CARExo with exogenous cargoes, miR-34a and doxorubicin were transfected by electroporation. The amounts of Exo/CARExo were $1\times10^{1}$ (measured by NTA) were mixed with miR-34a in buffer before electroporation. After electroporation, Exo/CARExo were set aside for an hour at 37° C. Then, mixed with 1 mg Doxorubicin, reacted at 37° C. for 60 min, then switched to 4° C. for 30 minutes, and then added 20 μL ExoQuick-TC (System Bioscience) was mixed well and reacted at 4° C. for 16 hours. After the reaction, centrifuge at 1500×g for 30 minutes at 4° C., removed the supernatant by suction, add 200 μL PBS to wash and remove by centrifugation, repeat the above PBS washing twice, and finally added 100 μL PBS to evenly disperse the exosomes. When done, the number of Exo/CARExo was re-analyzed with NTA and how many Exo/CARExo were lost during drug delivery.

Biodistribution

The present invention evaluated the tumor-targeting effect of Exo/CARExo in vivo using a tumor xenograft mouse model (NOD/SCID gamma mice). PBS, Exo, and CARExo were injected via the tail vein of 100 μL ($5\times10^{10}$ Exo/CARExo). The mice were scanned at different time-points and scarified at 24 h.

In Vivo Anti-Tumor Effects

A xenograft-tumor model was generated by injecting 0.1 mL of a MDA-MB-231 cell suspension ($5\times10^{6}/100$ L) into the right flank NOD/SCID gamma (NSG) nude mice. Mice bearing established MDA-MB-231 tumors (150-200 mm$^{3}$) were randomly sorted into groups, and the groups were treated as follows: (i) PBS, as a control; (ii) Exo-miR; (iii) Exo-Drug; (iv) Exo-Drug-miR (the drug equivalent was 5 mg/kg and miR equivalent was 0.1 nmoL/kg). The drugs were injected weekly through the tail vein for 7 consecutive weeks. The mice were weighed, and the tumors were measured with a caliper every 4 days. Tumor volumes were calculated using the following equation: tumor volume= (length×width×width)/2.

Tissue Collection and Hematoxylin-Eosin (H&E) Staining

The mice were anesthetized using an intraperitoneal injection of an aqueous chloral hydrate solution (3% w/v), at a dose of 1 mL/kg. They were then sacrificed, samples of blood were taken and their abdominal cavities were exposed. Liver, lung, spleen, heart and kidney samples were collected and stored temporarily in 10% neutral buffered formalin (NBF) prior to hematoxylin-eosin staining.

NBF (pH 7.2-7.4) was prepared from 100 mL of a 40% v/v solution of formaldehyde in water, anhydrous disodium hydrogen phosphate (6.5 g), sodium dihydrogen phosphate (4.0 g) and distilled water (900 mL). Liver, spleen, lung, heart and kidney tissues were recovered from the 10% NBF solution. Tissue slices were dehydrated, embedded in paraffin, cut and stained using hematoxylin and eosin.

3D Spheroids Model Construction

All cells were cultured in their respective appropriate medium. The culture medium was changed every 2 or 3 days. Prior to the decellularized lung ECM-embedding culture, the present invention harvested each cell type by treating with a solution of 0.25% trypsin in EDTA (Gibco), collected the cells by centrifugation at 1200 rpm. for 10 min and then dispersed the cells in each culture medium. The cell suspensions were mixed with the pre-gel solutions (4 wt %) of ECM to a final concentration of $5\times10^{6}$ cells ml$^{-1}$ for various cells. The aliquots of each cell-encapsulated pre-gel solution were transferred to the wells of a multi-well plate and placed in the incubator at 37° C. for 1 h. After gelation, the culture medium for the cancer or endothelial cells was added to the wells. Each culture medium was changed every 2 or 3 days.

Preparation of the Cell-Laden FGelMa Hydrogel with an Auxetic Structure

Figure 16A:
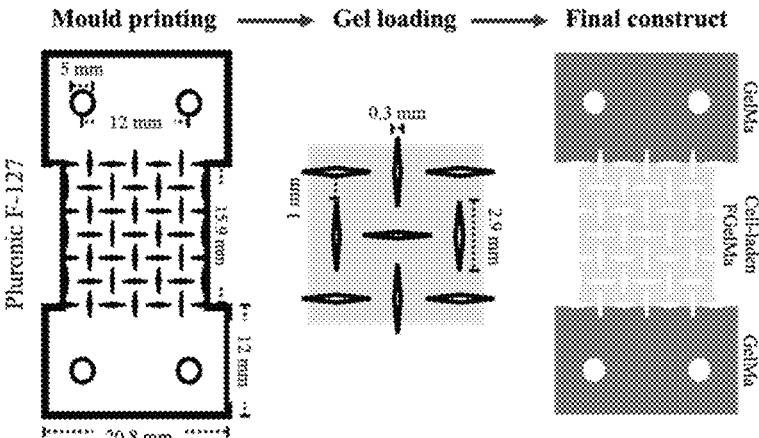
Figure 16A:
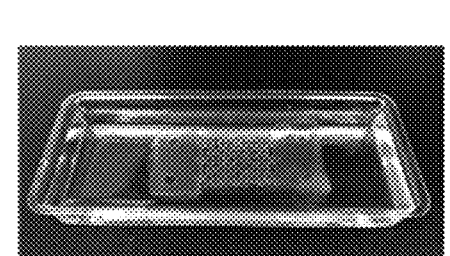
Figure 16A:
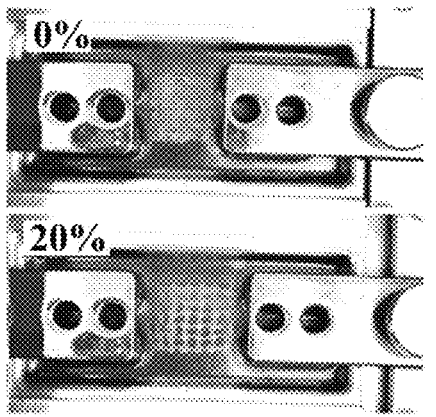

In the present invention, hydrogels with an auxetic structure were fabricated through a template moulding process. Considering that the cell-laden hydrogels with an auxetic structure should be compatible with a tensile bioreactor, three components were used to produce the construct: a Pluronic F-127 solution, GelMa, and cell-laden FGelMa. A positive mould was designed and printed using the BioX bioprinter (Cellink, Sweden) with the Pluronic F-127 (Sigma-Aldrich) solution at a concentration of 30 wt % in distilled water. FIGS. 16A-16C shows a representative unit cell of the auxetic construct. For the mould printing, the stereolithography (STL) model was designed and developed using SolidWorks. The STL file was then converted into a g-code file, which was used to determine the movements and printing paths of the bioprinter, using sliver software. After housing the fugitive ink in a syringe barrel equipped with a luer-locked nozzle with an inner diameter of 150 μm, the fugitive ink was deposited on a glass slide by applying a pneumatic pressure at 170 kPa to form a filament with diameter of approximately 250 μm, using a syringe moving speed of 25 mm/s. The fugitive mould of the auxetic construct was fabricated layer-by-layer (150 μm per layer) until the final thickness of the construct reached 2.1 mm. Next, warm (37° C.) PBS containing 15 wt % GelMa and 0.5 wt % 1-2959 was loaded into the mould to form a fixation portion with two openings on each side that could be connected to the tensile bioreactor (ATMS Boxer QQA Cyclic Stretch Culture System, Genemessenger, Kaohsiung, Taiwan) (FIG. 16A). The cell-laden FGelMa was obtained by mixing the HEK293T (or other normal cell lines and primary cells) with 10 wt % FGelMa in PBS containing 0.5% I-2959. The confluent cells cultured in cultured medium were trypsinized, centrifuged, and resuspended in the warm FGelMa solution at a density of $5 \times 10^6$ cells/mL. The cell-laden hydrogel was then loaded into the auxetic portion of the specimen. The specimens were incubated at 37° C. for 1 min to liquify the GelMa and FGelMa. After being exposed to the UV irradiation (365 nm) for 90 s, the specimens were soaked in cold (4° C.) PBS for 10 min to dissolve the fugitive F-127 (FIG. 16B). To apply cyclic tension, the specimen was fixed in the tensile bioreactor and supplied with 8 mL of culture medium; 20% of tensile strain was continuously applied to the cell-laden hydrogel at a frequency of 0.48 Hz during the culture period. The specimens cultured under static conditions served as the control group (FIG. 16C). All in vitro experiments were conducted in a cell culture incubator with 5% $CO_2$ and 100% humidity at 37° C.; whereas the culture medium was refreshed every 2 days.

The synthesis and characterization of FGelMa, and the design and applying of the tensile bioreactor are described in Yi-Wen Chen et al., (Materials & Design, Volume 195, October 2020, 108982) which is incorporated by reference herein in its entirety.

Treatment of YAP Inhibitor YAP

In the earlier results, the present invention considered that the presence of tensile stimulation of HEK293T was through the activation of cells YAP protein, a mechanosensitive transcriptional activator with a critical role in the cell behaviors. Thus, in the end, the present invention exposed the HEK293T-laden auxetic scaffold to a YAP inhibitor, Verteporfin (MedChemExpress, Monmouth Junction, NJ, USA). After culturing for certain days, the present invention used immunofluorescence staining and osteogenic-related proteins to assess the role of YAP in tensile stimulation.

Result

Figure 1B:
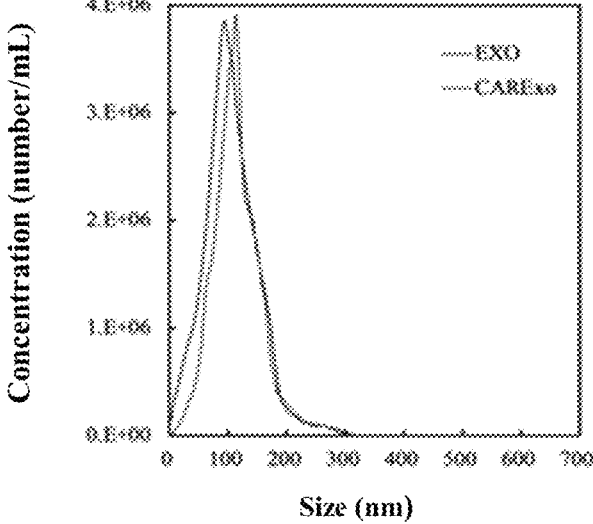

Exosome characteristics with/without cargo engineering were verified. The morphology results were seen in TEM images of the Exo and CARExo isolation from tangential flow filtration (TFF) technology. The results showed exosome size similar levels even through cargo engineering (FIG. 1A). They displayed clearly the vesicle hollow feature and surface membrane. The NTA analysis showed that the main peak of the diameters at 110 nm (Exo) and 120 nm (CARExo), separately (FIG. 1B). These results proved the exosome morphology remains stable after cargo engineering treatment.

Figure 2A:
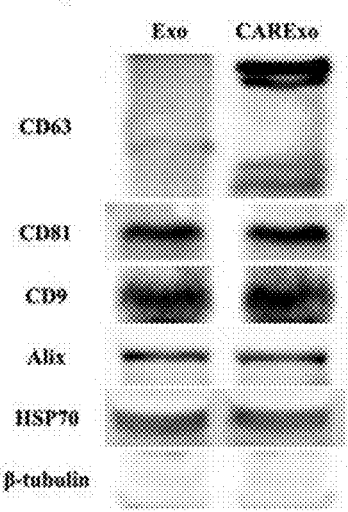
FIGS. 2A-2B show the biomarker identification of exosomes by using west blot (CD63, CD81, CD9, Alix, HSP-70 and β-tubulin) and flow cytometry.
Figure 2B:
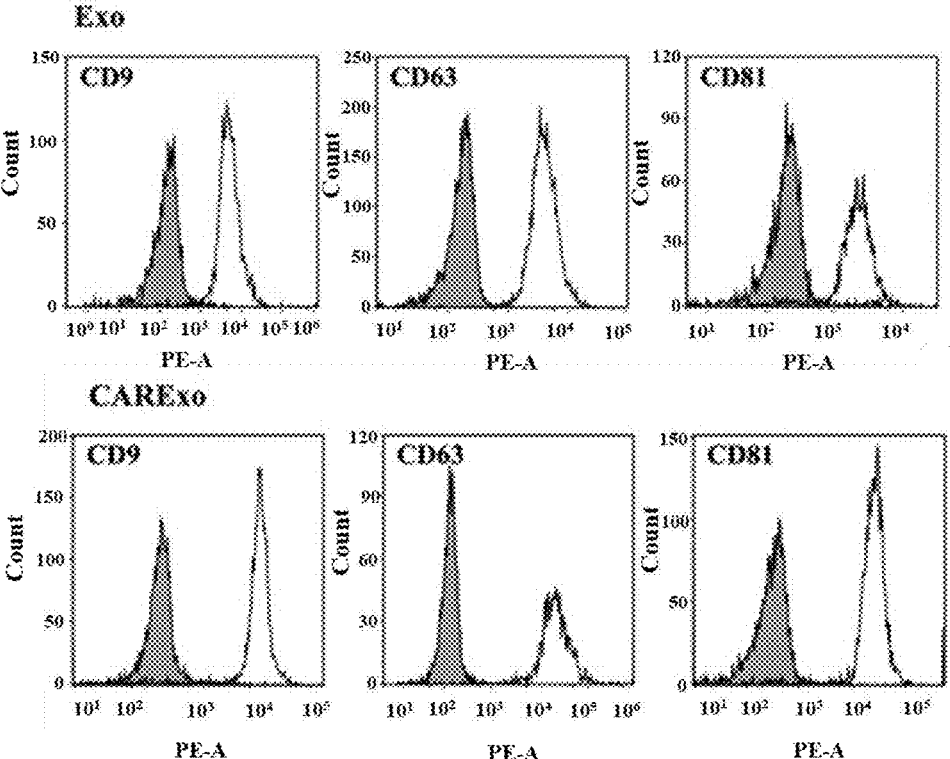

The presence of CD9, CD63, CD81, HSP71 and Alix which were commonly enriched on the exosome surface membrane were analyzed by using Western blotting analysis with anti-CD9, anti-CD63, anti-CD81, anti-HSP70, and anti-Alix (FIG. 2A). The cytosolic marker 3-tubulin was absent in exosome. The results of the present invention showed CARExo had the same exosome characteristic marker expression. Flow cytometric analysis showed that levels of the exosome marker CD9, CD63, and CD81 were detected in Exo group (FIG. 2B). In addition, the surface modification of exosomes by cargo engineering did not affect the performance of the parental exosomes.

Figure 3:
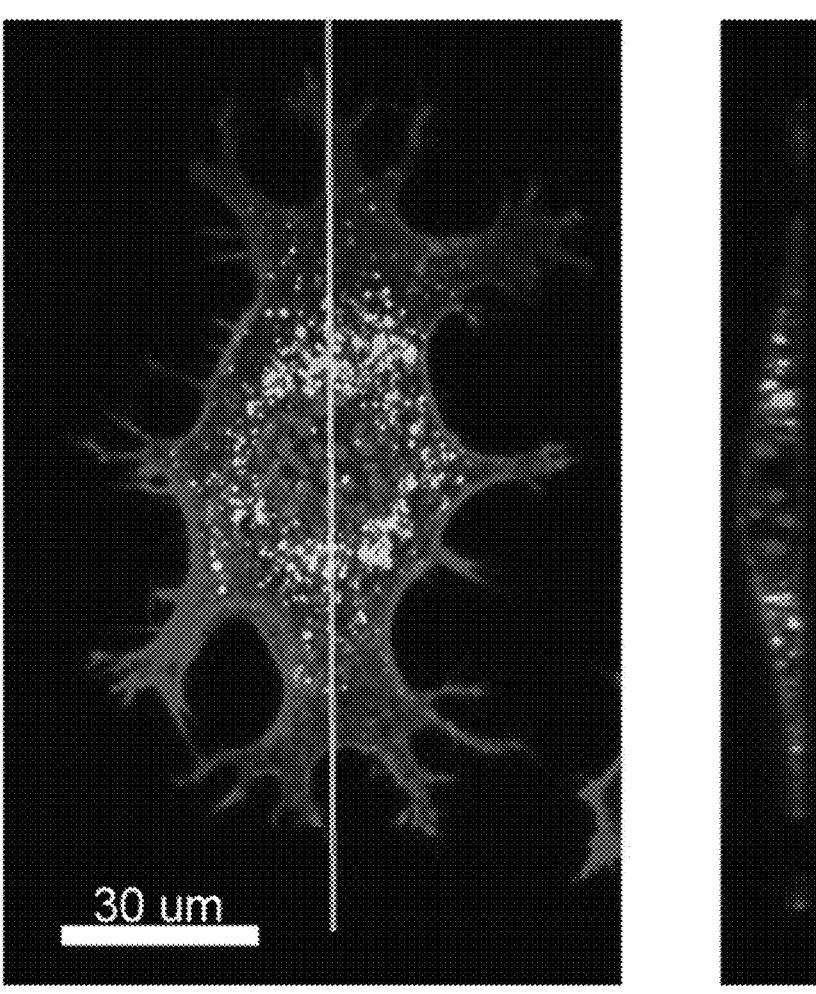
FIG. 3 shows the assessment of exosome (green) retention inside MDA-MB-231 cells (F-actin: red, nuclei: blue) using confocal microscopy. Exosome: green, F-actin: red, and nuclei: blue.

Numerous studies have shown that exosomes can be used as an ideal cargo for therapeutic effects on specific cell targets (FIG. 3). Therefore, the present invention further studied the uptake of CARExo in MDA-MB-231 nucleus. Exosome tracker reagent PKH67 (green) was used to stain CARExo, and then it was co-cultured with MDA-MB-231 for 24 h. Then, in the present invention, F-actin cytoskeleton reagent (Red) and nucleus regents DAPI (Blue) were further used to stain, and the images showed the exosome was uptaken in nucleus layer (YZ section) via confocal microscopy. Thus, it was vital clues that the CARExo was high potential for precision therapy in cancer.

Figure 4:
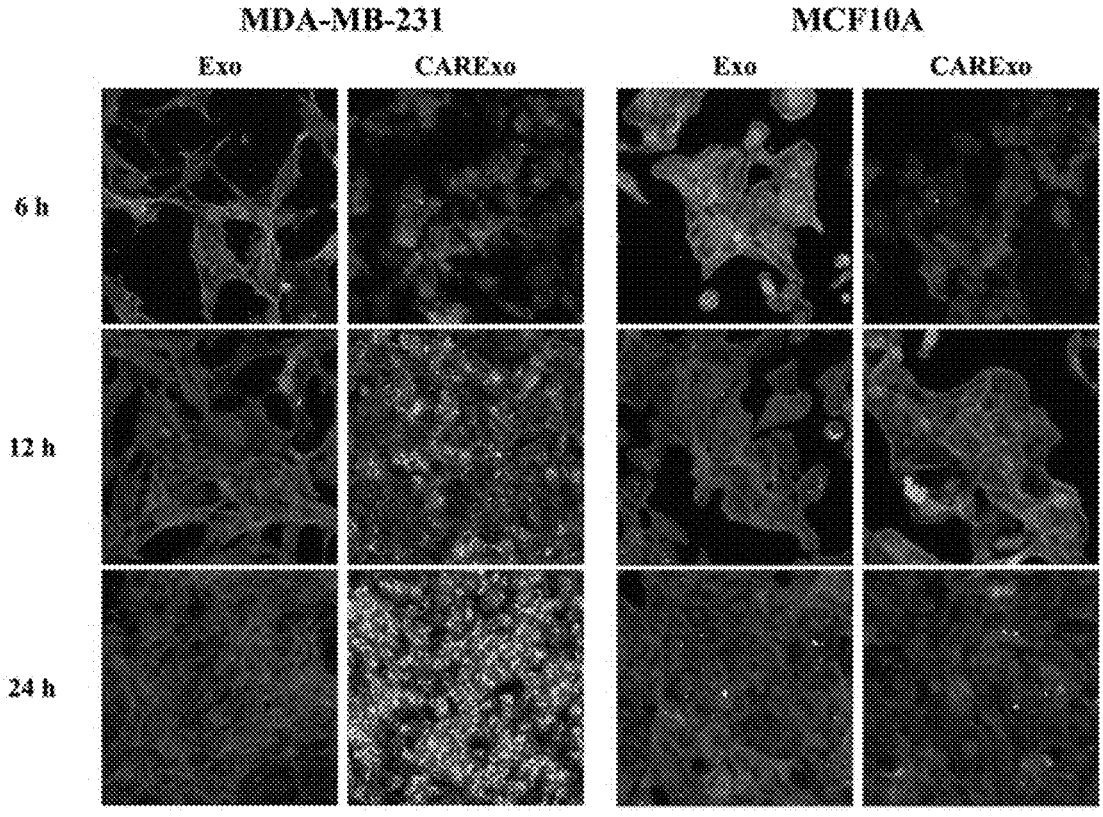
FIG. 4 shows the comparison of uptake effect of exosomes with/without target function in breast cancer cells (MDA-MB-231) and normal breast cells (MCF-10A) using fluorescent staining. Exosome: green, F-actin: red, and nuclei: blue.

Additionally, to further confirm CARExo could specifically target breast cancer (MDA-MB-231), the present invention used normal breast cell (MCF10A) for comparison (FIG. 4). MDA-MB-231 and MCF-10A were incubated with Exo and CARExo separately at different time points, after 6 h, 12 h, and 24 h, immunofluorescence detection was conducted. The results showed that the 231 cells had a good affinity for CARExo. After 12 hours, a large amount of CARExo could be uptake, while the amount of Exo was relatively small.

Figure 5:
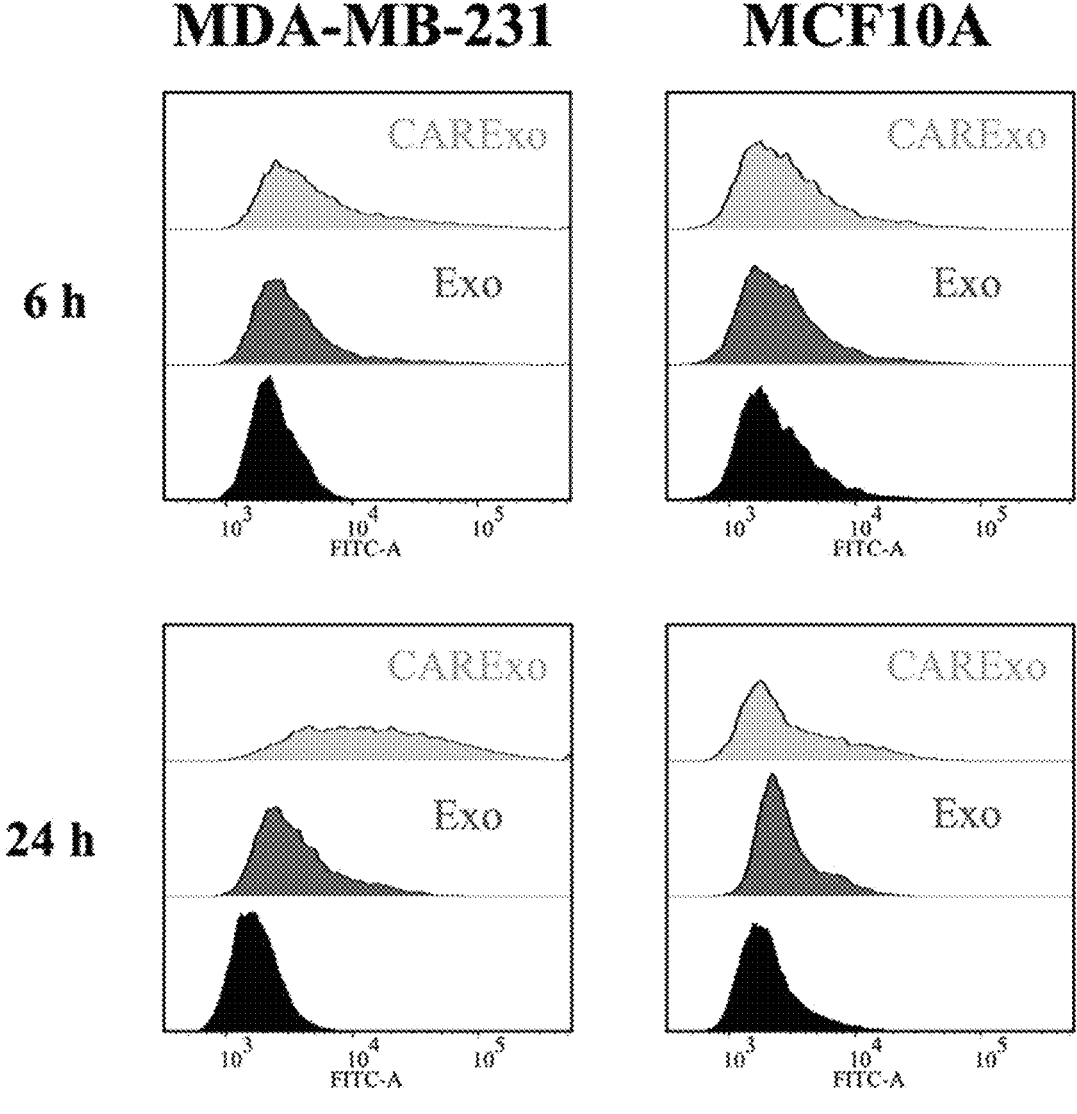
FIG. 5 shows the comparison of uptake effect of exosomes with/without target function by breast cancer cells (MDA-MB-231) and normal breast cells (MCF-10A) using flow cytometry.

The exosome target rate was measured by flow cytometry. MDA-MB-231 and MCF-10A treated with CARExo and Exo for 6 h, and 24 h (FIG. 5). In 6 h, there were no difference expression in two groups. However, treated with CARExo for 24 h, the present invention detected a major increase in the MDA-MB-231 subpopulations, whereas Exo had little change. The CARExo precisely targeted MDA-MB-231 and was more effective than MCF-10A.

Figure 6:
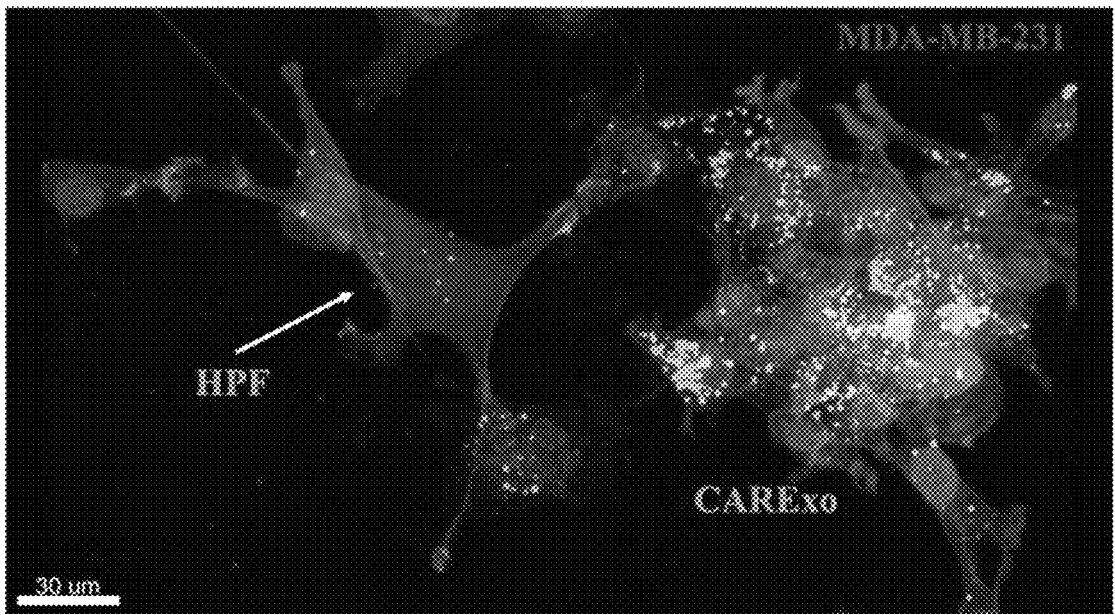
FIG. 6 shows the comparison of uptake effect of targeting exosomes by breast cancer cells (MDA-MB-231) and normal breast cells (MCF-10A) in co-culture system using fluorescent staining. Exosome: green, F-actin: red, and nuclei: blue. HPF: human pulmonary fibroblasts.

In the experiment of co-culturing CARExo with cancer cells (MDA-MB-231, red) and normal cells (HDF, light green), it could also be found that CARExo (green) was concentrated in cancer cells, which can further confirm that the CARExo had specificity for cancer cells (FIG. 6).

Figure 7:
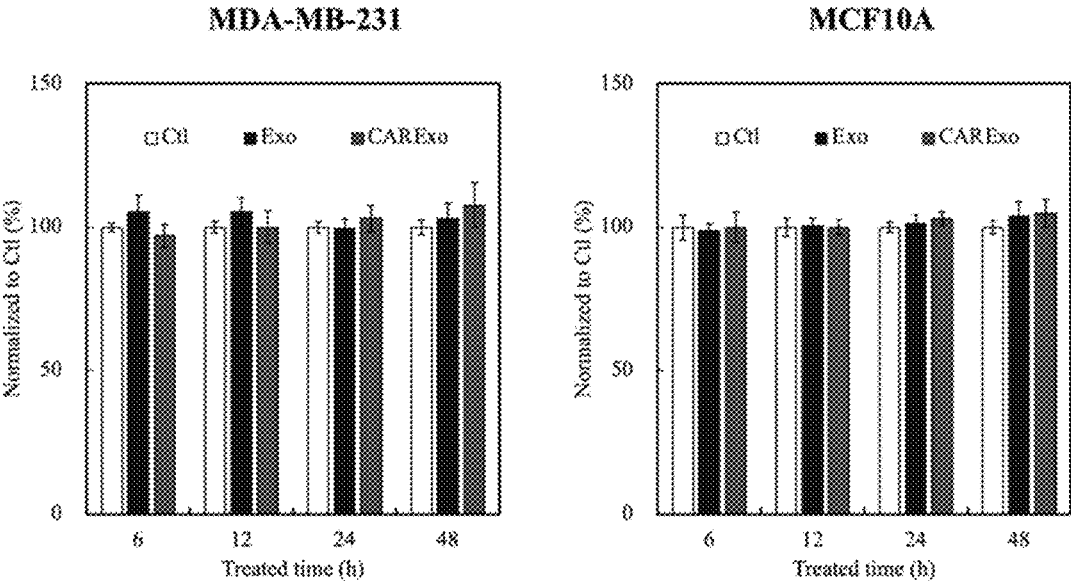
FIG. 7 shows the evaluation of the cytotoxicity of exosomes with/without target function to breast cancer cells (MDA-MB-231) and normal breast cells (MCF-10A). Ctl: Control.

FIG. 7 shows the evaluation of the cytotoxicity of CARExo, Exo, and Control (Ctl) on MD-NMBA-231, MCF 10A cells. After 6, 12, 24, 48 hours of co-culture, it showed no matter CARExo or Exo, the quantification of cell survival demonstrated that these exosomes have none cytotoxicity. The results were representative of three independent experiments.

Figure 8:
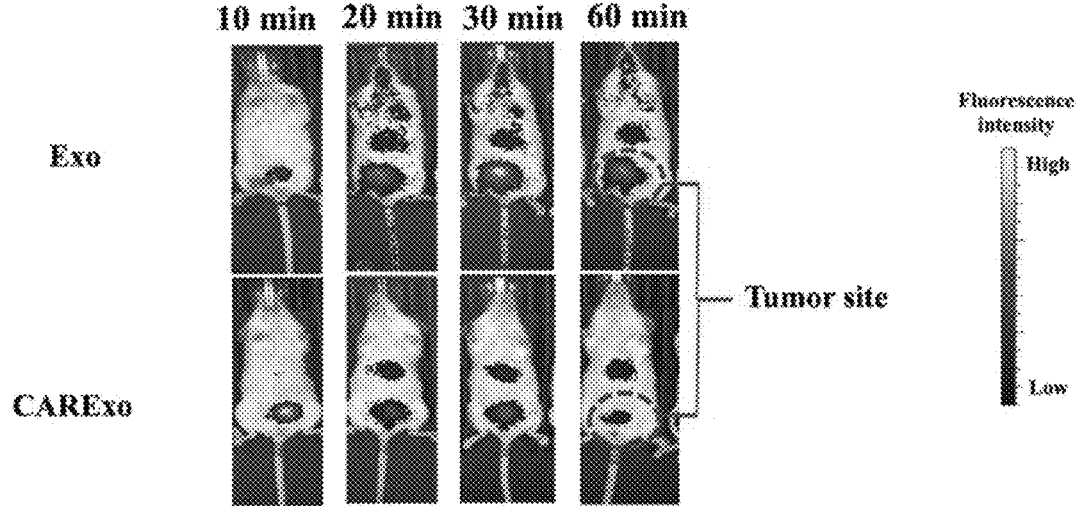
FIG. 8 shows the evaluation of the bio-distribution in vivo therapeutic potential of CARExo. The present invention constructs a xenograft mouse model by using MD-MBA-231cells.

To further evaluate the bio-distribution in vivo therapeutic potential of CARExo, the present invention constructed a xenograft mouse model by using MDA-MB-231cells (FIG. 8). Consistent with the in vitro results, CARExo significantly targeted the tumors, so few signals were detected in the lung and spleen, which were normal exosome storage locations.

Figure 9:
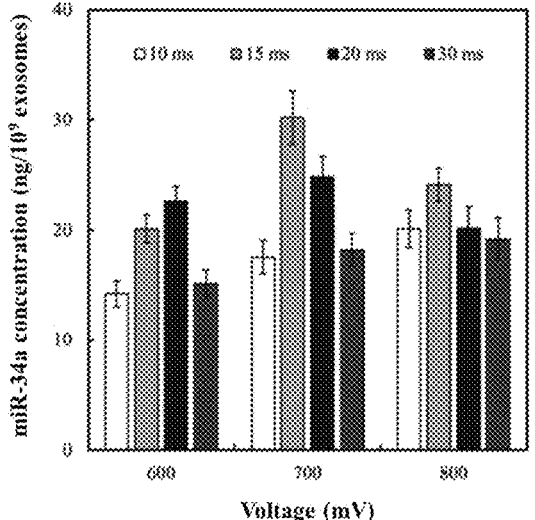
FIG. 9 shows the amount of miRNA and DOX co-loaded in exosomes. DOX: doxorubicin.
Figure 9:
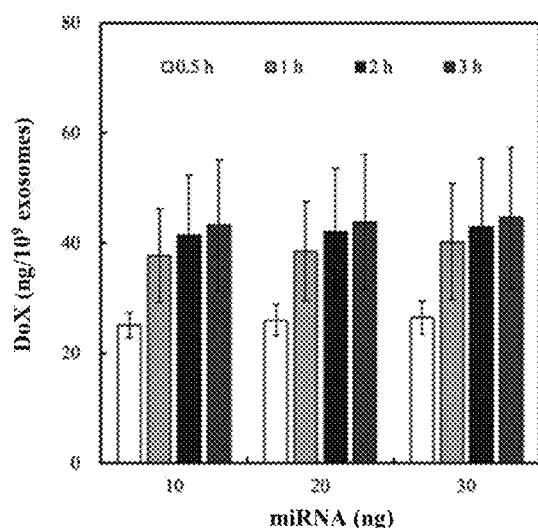

Additionally, the ideal electroporation parameter ranged from 600 mV ~800 mV, which allowed exosome to carry miR-34a stably (FIG. 9). The result showed 700 mV has the best delivering efficiency, and CARExo could detect 30 ng miR-34a, suggesting this covering efficiency was high potential applied in drug delivery. CARExo delivered the cancer targeting drug doxorubicin (Dox) with high efficiency at 700 mV. The result further indicated excellent efficiency when Dox was delivered together with 20 ng miR-34a. The above results showed that this electroporation parameter can make the exosomes stably carry two drugs at the same time.

Figure 10:
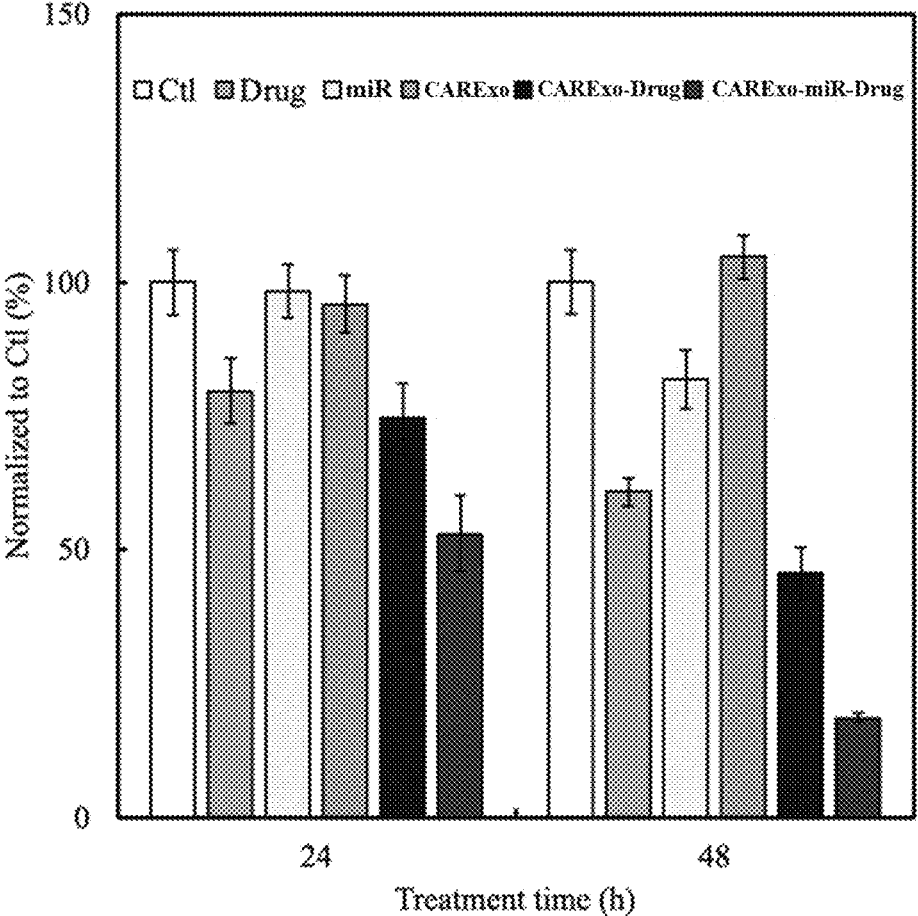
FIG. 10 shows the evaluation of the cytotoxicity of exosomes loaded with miRNA and DOX on MDA-MB-231. Ctl: Control.

Then, the present invention further increased the test group to six groups: Ctl, Drug, miR, CARExo, CARExo-Drug and CARExo-miR-Drug, to distinguish the validation of cancer cell killing efficacy (FIG. 10). After 24 h and 48 h, the Exo-miR-Drug had the best cell killing than other groups. Whereas CARExo or Drug only the effect was about 50%. It could be seen that the cocktail of exosomes can effectively and quickly kill cancer cells in the first time.

Figure 11:
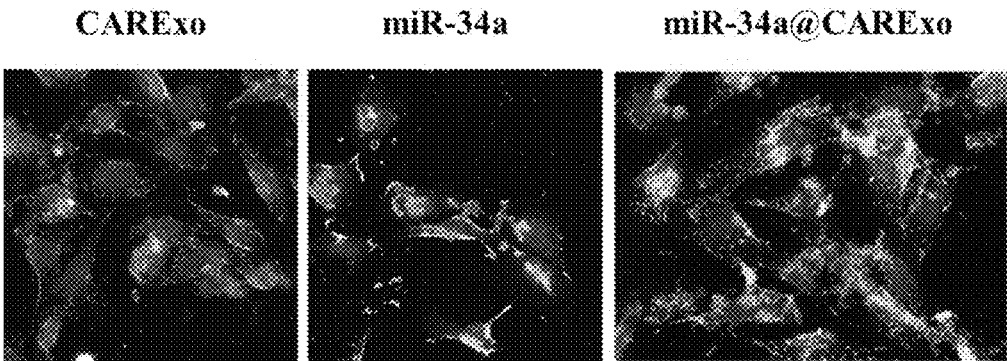
FIG. 11 shows the evaluation of the effect of miRNA-loaded exosomes (miR-34a@CARExo) on miRNA release inside cells by fluorescent staining.

Then, the present invention stained with CARExo and miR-34a tracker, respectively (FIG. 11). As expected, this again verifies that CARExo (green) encapsulated miR-34a (red) that could present co-localization phenomenon.

Figure 12A:
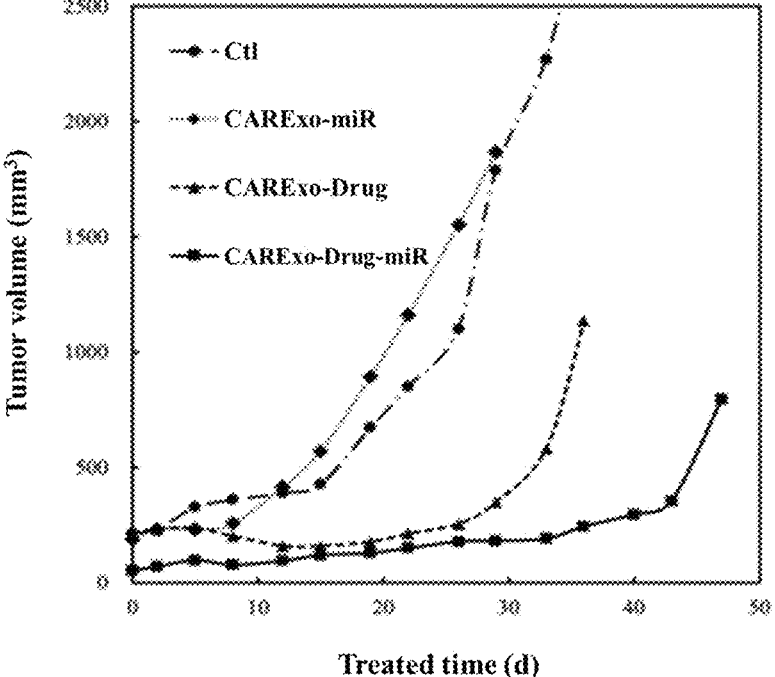
FIGS. 12A-12B show the validation of the efficacy of miRNA/DOX-loaded CARExo in inhibiting breast cancer tumors in vivo and evaluating tumor metastasis to other organs.
Figure 12B:
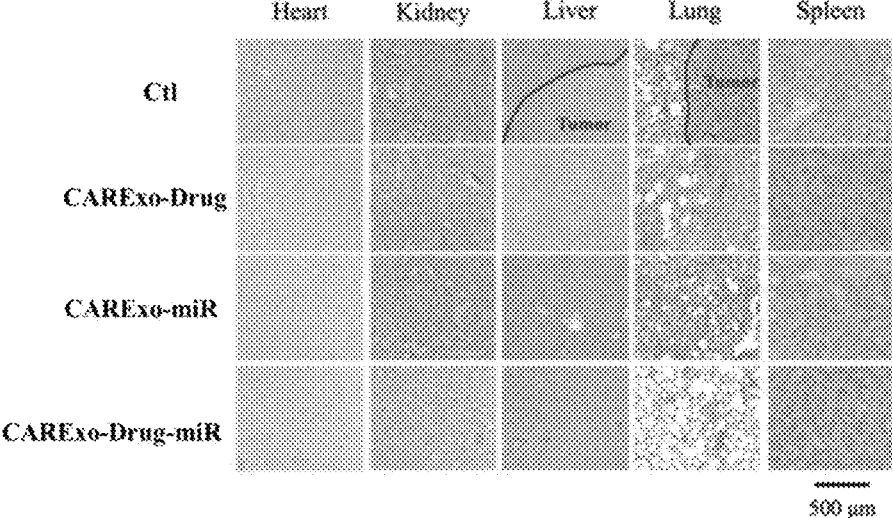

The present invention wanted to further demonstrate that CARExo exosomes had an additive effect on tumor suppression in vivo (FIGS. 12A-12B). The present invention designed the four groups: control (Ctl), CARExo-miR (cargo exosome loaded with miR-34a), CARExo-Drug (cargo exosome loaded with doxorubicin), and CARExo-Drug-miR (cargo exosome loaded with miR-34a and doxorubicin). Through animal experiments, CARExo-Drug-miR was subcutaneously injected into mice and observed at different time points. It was found that the inhibitory effect on tumor formation was better than that of other groups (FIG. 12A). Tumor volume and weight were significantly reduced in CARExo-Drug-miR. Then, the present invention wanted to confirm the cytotoxicity to other organs. The therapeutic test focused on liver and lung, and other organs including heart, kidney, and spleen. HE stains showed that the above organs retained original morphology (FIG. 12B). It proved that CARExo-Drug-miR was safe and precise target on tumor site.

Figure 13:
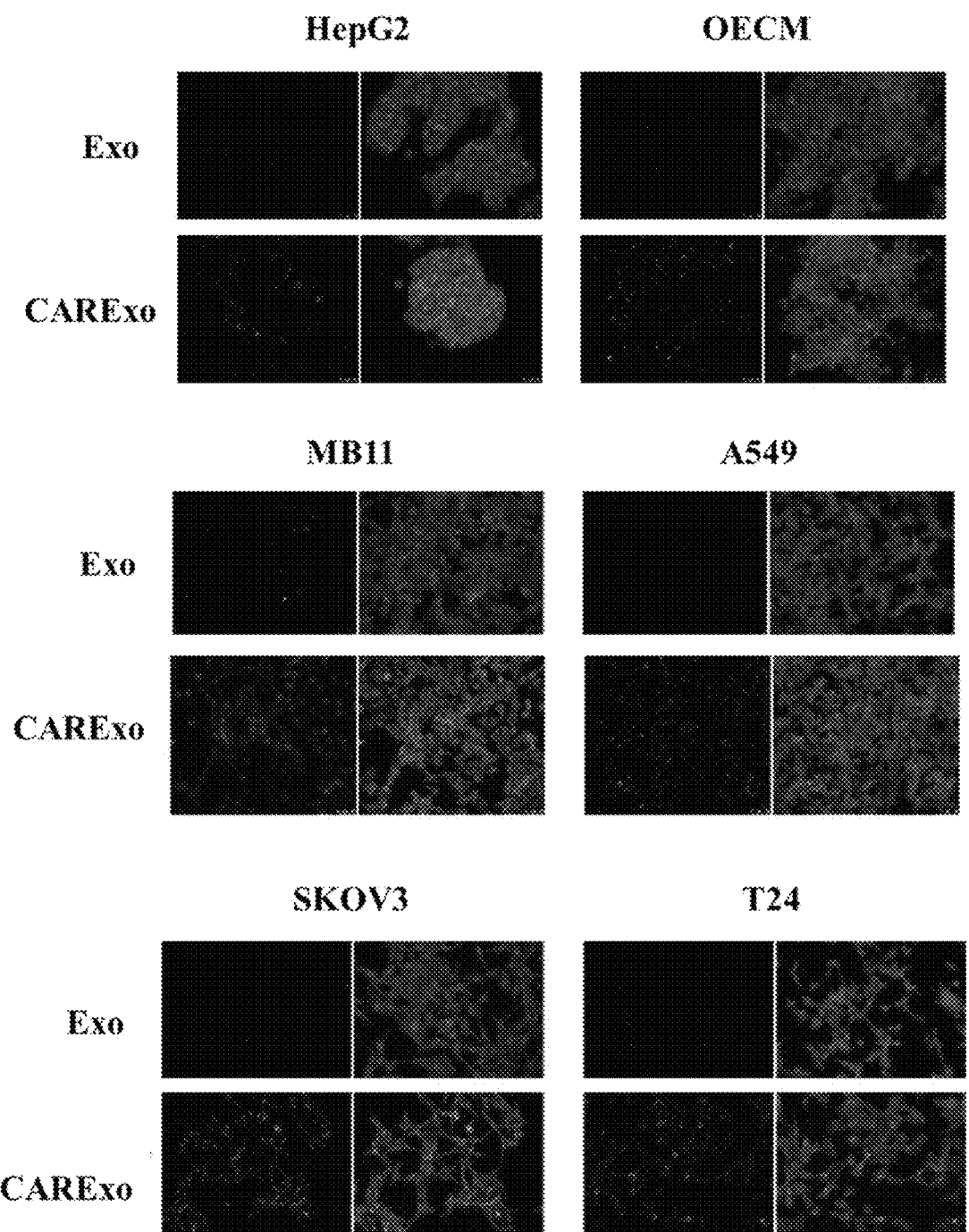
FIG. 13 shows the comparison of uptake effect of exosomes with/without target function in MB11(glioblastoma), A549 (non-small cell lung cancer), HepG2 (hepatocyte carcinoma), OECM (oral squamous carcinoma), SKOV3 (ovarian cancer cell line), and T24 (urinary bladder carcinoma) using fluorescent staining. Exosome: green, F-actin: red, and nuclei: blue.

In FIG. 13, the present invention also tested the CARExo efficacy with different cancer models: MB11(glioblastoma), A549 (non-small cell lung cancer), HepG2 (hepatocyte carcinoma), OECM (oral squamous carcinoma), SKOV3 (ovarian cancer cell line), and T24 (urinary bladder carcinoma).

Figure 14:
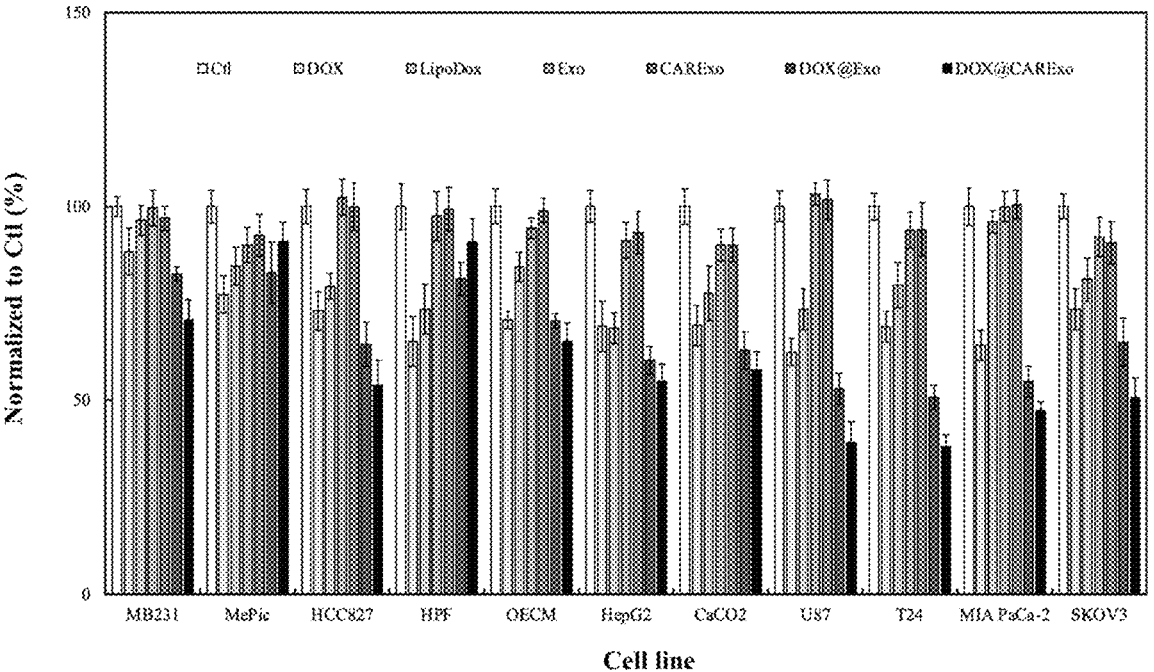
FIG. 14 shows the comparison of the cytotoxicity of DOX-loaded exosomes with/without target function in breast cancer (MB231), lung cancer (HCC827), oral cancer (OECM), liver cancer (HepG2), colorectal cancer (CaCO2), medulloblastoma (U87), urinary bladder carcinoma (T24), pancreatic cancer (MIA PaCa-2), and ovarian adenocarcinoma (SKOV3). Mammary epithelial cells (MePic) and human pulmonary fibroblasts (HPF) are normal cell.

In addition, the present invention designed the seven groups, control (Ctl), DOX (doxorubicin), LipoDox (liposome loaded with doxorubicin), Exo (exosome), CARExo (cargo exosome), DOX@Exo (exosome loaded with doxorubicin) and DOX@CARExo (cargo exosome loaded with doxorubicin), to test different cancer cell lines. Similar results could be seen in different cancer cell lines (FIG. 14). In addition to breast cancer (MB231), there were also lung cancer (HCC827), oral cancer (OECM), liver cancer (HepG2), colorectal cancer (CaCO2), pancreatic cancer (MIAPaCa-2), medulloblastoma (U87), urinary bladder carcinoma (T24) and ovarian adenocarcinoma (SKOV3) etc. It could be found that DOX@CARExo could show good cytotoxicity. In addition, in normal cells, the cytotoxicity of CARExo was also lower than that of DOX and Lipo-DOX.

Figure 15:
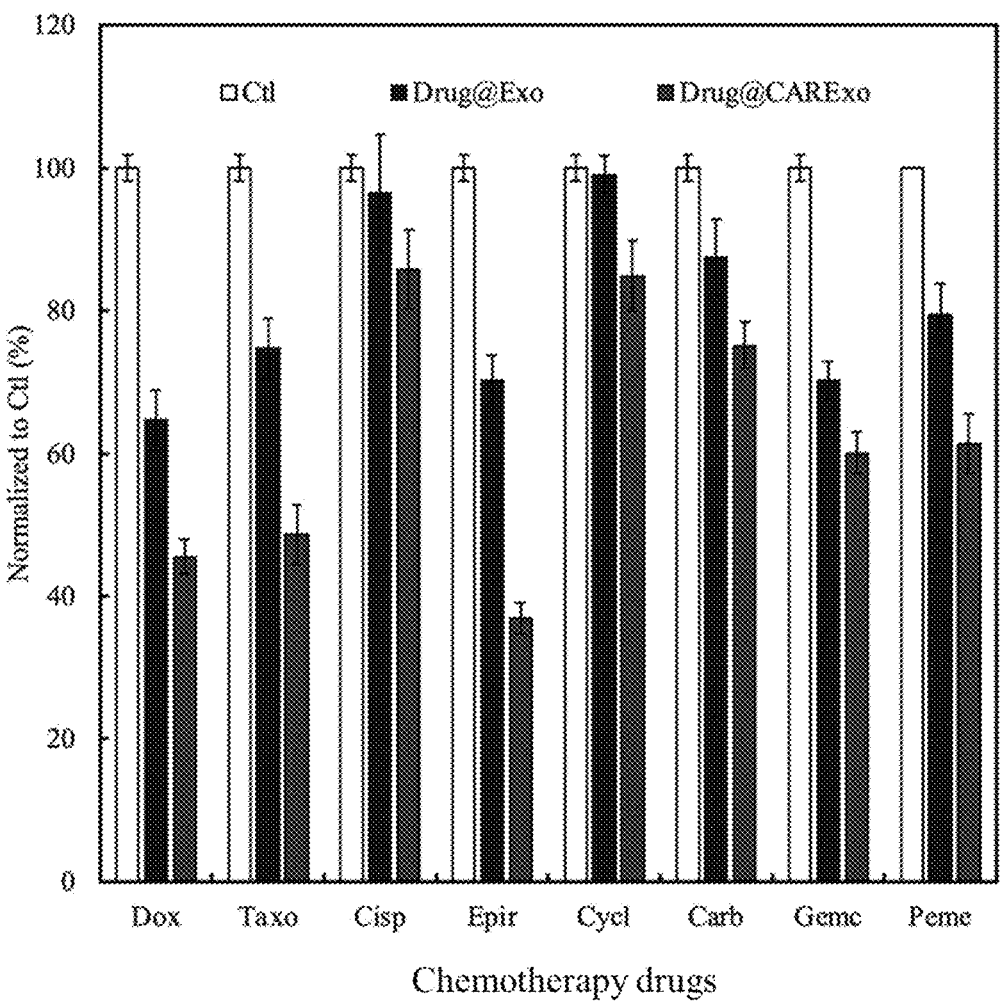
FIG. 15 shows the comparison of the cytotoxicity of various chemo drug-loaded exosomes with/without target function in breast cancer (MB231). Ctl: Control.

In addition, the present invention could also carry different chemotherapeutic drugs (e.g. doxorubicin (DOX), taxotere (Taxo), cisplatin (Cisp), epirubicin (Epir), cyclophosphamide (Cycl), carboplatin (Carb), gemcitabine (Gemc), and pemetrexed (Peme)) through exosomes and serve as carriers to kill cancer cells (FIG. 15). The results showed that the chemotherapeutic drugs loaded on CARExo were more effective in killing cancer cells (MDA-MB-231) than Exo, which also had the same trend as the previous results with DOX.

Figure 17:
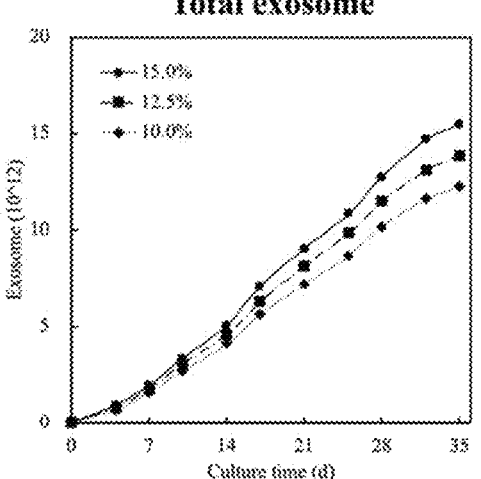
FIG. 17 shows the comparison of the yield of exosomes produced by HEK293T-laden auxetic scaffolds in tensile culture system and the yield of exosomes secreted by single cell.
Figure 17:
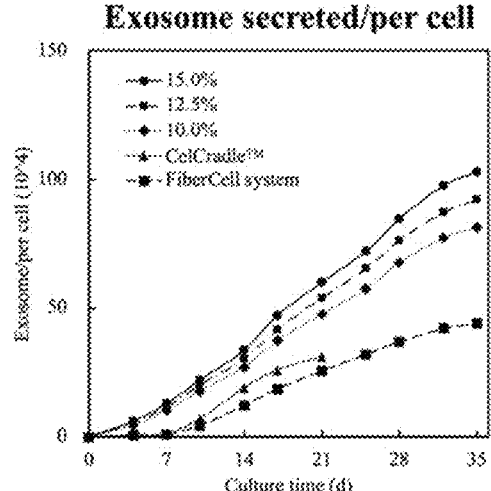

The hydrogel scaffold with different concentration (10%, 12.5%, and 15%) had been treated cyclic tensile stress for different time-points, there was a noticeable change in the efficiency of exosome secretion (FIG. 17). In 15% FGelMa scaffold, the exosome was released more than 12.5% and 10%. In addition, the present invention also assessed the efficiency of exosome secretion per cell. After cyclic tensile treatment for 1 month, the exosome secretion was about $1.03 \times 10^6$/per cell, $0.92 \times 10^6$/per cell, and $0.81 \times 10^6$/per cell in 15%, 11.5%, and 10% FGelMa hydrogel scaffold, respectively. The present invention also compared this experiment with bioreactors on the market that are specialized in the production of exosomes. From the results, it could be found that the FiberCell system could collect exosomes continuously for a long time, but the yield after one month was about $0.44 \times 10^6$/per cell, which was much smaller than the system of the present invention. The other CelCradle™ was a kind of bioreactor similar to suspension culture. It could not collect exosomes for long term, so it could only be tested for about two weeks, and the yield was also smaller than the system of the present invention.

Figure 18:
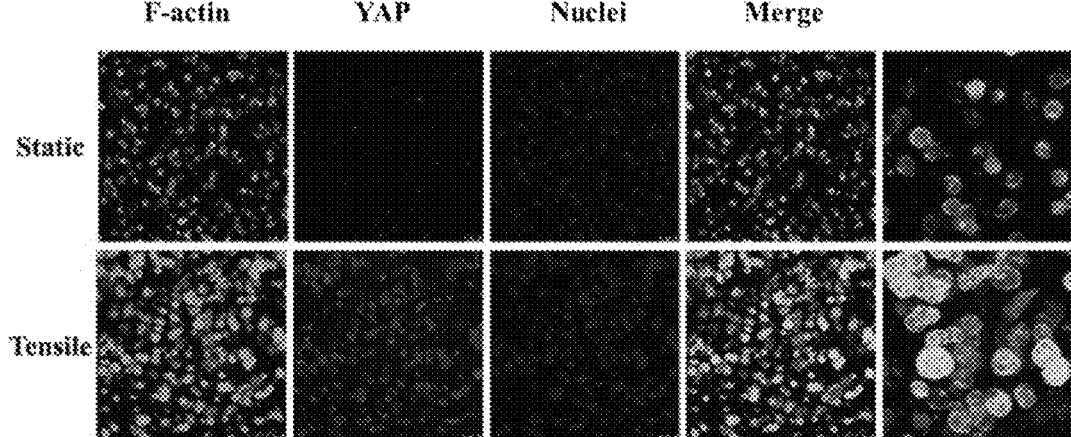
FIG. 18 shows the differences in cell morphology and YAP protein staining of HEK293T-laden auxetic scaffolds in a cyclic tensile culture system.

The present invention additionally used fluorescent staining of cytoskeleton (F-actin, green), mechanosensing marker (YAP, red), and nuclei (blue) to identify changes in cell encapsulated of hydrogel scaffold upon stretching stimulation (FIG. 18). As shown in the FIG. 18, after the cells were stretched with cyclic tensile for 3 days, it could be found that the cells will change from single cells to self-assembled three-dimensional cell spheroids, while the cells in the static culture group were still single-cell. And three-dimensional cell spheroids formed by mechanical force stimulation would express a large amount of YAP protein around the spheroid, while statically cultured cells hardly expressed it, so the present invention speculated that the mechanical force stimulated cells to express a large amount of YAP protein and made that the secretion of exosomes was enhanced after the formation of 3D spheroids.

Figure 19A:
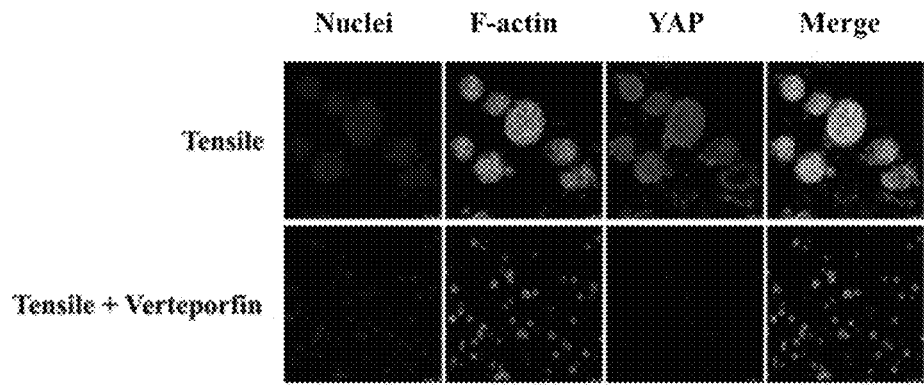
FIGS. 19A-19B shows the differences in cell morphology, YAP protein staining, and exosome secretion of HEK293T-laden auxetic scaffolds with YAP inhibitor (Verteporfin) in a cyclic tensile culture system.
Figure 19B:
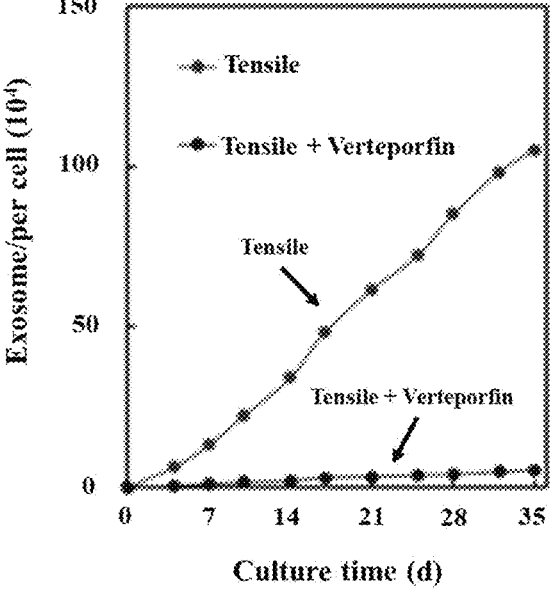

Subsequently, an inhibitor of YAP protein (Verteporfin) was added in the process of cyclic tensile stimulation. From fluorescent staining, it was shown that in the group without the addition of the inhibitor, the expression of YAP protein, the morphology of cell spheroids, and the amount of exosome secreted were consistent with the previous results (FIG. 19A). The cell morphology in the group with added inhibitors were single cells that could not self-assemble to form three-dimensional spheroids, which were similar to statically cultured cells, and the secretion of exosomes was also greatly reduced to 5% of the cyclic tensile stimulation group (FIG. 19B). Therefore, it was speculated that under three-dimensional culture, continuous mechanical stimulation could make cells form three-dimensional spheres by activating YAP protein, and greatly increased the secretion of exosomes.

Figure 20:
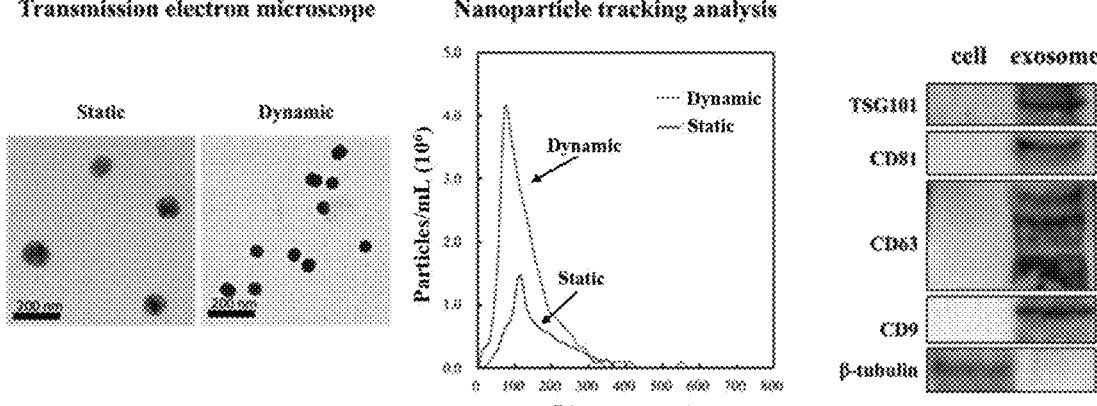
FIG. 20 shows the differences in morphology, size, and biomarkers of HEK293T-related exosomes between static and dynamic culture system.

To confirm the appearance of exosomes secreted by cells after static/dynamic stretching, the present invention isolated extracellular vesicles by a standard TFF protocol (FIG. 20). Transmission electron microscopy and Nanosight size distribution analysis demonstrated a population of small circular particles between 50 to 350 nm, and the main peak at 122 nm. Western blot analysis demonstrated a striking enrichment of the tetraspanin exosomal markers CD9, CD63, CD81, TSG101 and cytosolic marker β-tubulin under dynamic stretch. A more modest enrichment of another exosomal marker, CD9, CD63, CD81, TSG101 were seen under static stretch. In combination, these results confirmed successful isolation of exosome-like particles from dynamic stretch.

Those who skilled in the art will understand the above concept as a description of the methods used to convey the deposited application information. Those one skilled in the art recognize that these are illustrative only and that many equivalents are possible.

---

---

What is claimed is:

1. A drug carrier, which comprises an exosome comprising a fusion protein, wherein the fusion protein is expressed on the membrane of the exosome and comprises a targeting protein and an exosomal transmembrane protein, the targeting protein comprises an anti-HLA-G protein, and the sequence of the anti-HLA-G protein comprises the peptide sequence of SEQ ID NO: 2, the exosomal transmembrane protein is connected to the targeting protein and used to express the targeting protein on the outside of the exosomal membrane, and the targeting protein is used to bind to HLA-G proteins expressed on cancer cells.

2. The drug carrier of claim 1, wherein the exosomal transmembrane protein is a transmembrane domain of CD9, CD63 or CD81.

3. The drug carrier of claim 1, wherein the exosome further comprises an anti-cancer agent.

4. The drug carrier of claim 3, wherein the anti-cancer agent is a chemotherapy agent or a microRNA for treating cancer.

5. A method for treating a subject with cancer, comprising administering a composition into the subject with cancer, wherein the composition comprises a therapeutic exosome, and the therapeutic exosome comprises a fusion protein and an anti-cancer agent, and the fusion protein is expressed on the membrane of the therapeutic exosome and comprises a targeting protein and an exosomal transmembrane protein, the targeting protein comprises an anti-HLA-G protein, and the sequence of the anti-HLA-G protein comprises the peptide sequence of SEQ ID NO: 2, the exosomal transmembrane protein is connected to the targeting protein and used to express the targeting protein on the outside of the therapeutic exosomal membrane, and the targeting protein is used to bind to HLA-G proteins expressed on cancer cells.

6. The method of claim 5, wherein the exosomal transmembrane protein is a transmembrane domain of CD9, CD63 or CD81.

7. The method of claim 5, wherein the cancer comprises breast cancer, lung cancer, oral cancer, liver cancer, colorectal cancer, glioblastoma, medulloblastoma, bladder cancer, pancreatic cancer, or ovarian cancer.

8. The method of claim 5, wherein the anti-cancer agent is a chemotherapy agent or a microRNA for treating cancer.

9. The method of claim 8, wherein the chemotherapy agent comprises doxorubicin, taxotere, cisplatin, herceptin, perjeta, epirubicin, cyclophosphamide, carboplatin, gemcitabine, or pemetrexed, or a combination thereof.

10. The method of claim 8, wherein the microRNA for treating cancer comprises miR-34a.

* * * * *

SEQUENCE LISTING

```
Sequence total quantity: 2
SEQ ID NO: 1          moltype = DNA  length = 405
FEATURE               Location/Qualifiers
source                1..405
                      mol_type = other DNA
                      organism = synthetic construct
SEQUENCE: 1
agcgctggtc acgtgcagct ggtggaaagc ggcggcggca gcgtgcaagc cggcggcagc   60
ctgaagctga gctgcgtgac aagcgcctac accttctccg ctagcggcaa ctgcatgggc  120
tggctgagac aagcccccgg caagggcaga gagggcatcg ccgccaccta cacaagaagc  180
gccaagacct actacgccga cagcgtgaag ggcagattca ccatcagcca agacaacgcc  240
aagaacaccg tgtacctgca gatgaacggc ctgaagcccg aggacaccgc cacctactac  300
tgcgccgtgg ctagatgcgc cggcagaccc gacagaagca ccctgacaag cttcgcctgg  360
tggggccaag gcacccaagt gaccgtgagc agcctggaga ccggt             405

SEQ ID NO: 2          moltype = AA  length = 135
FEATURE               Location/Qualifiers
source                1..135
                      mol_type = protein
                      organism = synthetic construct
SEQUENCE: 2
SAGHVQLVES GGGSVQAGGS LKLSCVTSAY TFSASGNCMG WLRQAPGKGR EGIAATYTRS   60
AKTYYADSVK GRFTISQDNA KNTVYLQMNG LKPEDTATYY CAVARCAGRP DRSTLTSFAW  120
WGQGTQVTVS SLETG                                                    135
```